(12) United States Patent
Burger et al.

(10) Patent No.: US 8,409,185 B2
(45) Date of Patent: Apr. 2, 2013

(54) REPLACEABLE AND/OR EASILY REMOVABLE NEEDLE SYSTEMS FOR DERMAL AND TRANSDERMAL CRYOGENIC REMODELING

(75) Inventors: Keith Burger, San Francisco, CA (US); Lisa Elkins, Menlo Park, CA (US); Ronald Williams, Menlo Park, CA (US)

(73) Assignee: Myoscience, Inc., Redwood City, CA (US)

( * ) Notice: Subject to any disclaimer, the term of this patent is extended or adjusted under 35 U.S.C. 154(b) by 1809 days.

(21) Appl. No.: 11/675,886

(22) Filed: Feb. 16, 2007

(65) Prior Publication Data

US 2008/0200910 A1 Aug. 21, 2008

(51) Int. Cl.
*A61B 18/18* (2006.01)
(52) U.S. Cl. .......................................... 606/24; 604/291
(58) Field of Classification Search ............... 606/20–23, 606/34; 600/439, 459
See application file for complete search history.

(56) References Cited

U.S. PATENT DOCUMENTS

| | | | |
|---|---|---|---|
| 2,319,542 A | 5/1943 | Hall |
| 2,672,032 A | 3/1964 | Towse |
| 3,226,492 A | 12/1965 | Steinberg |
| 3,343,544 A | 9/1967 | Dunn et al. |

(Continued)

FOREIGN PATENT DOCUMENTS

| | | |
|---|---|---|
| CA | 2 643 474 | 9/2007 |
| EP | 0043447 A2 | 6/1981 |

(Continued)

OTHER PUBLICATIONS

International Preliminary Report on Patentability of PCT Application PCT/US2006/019471, issued Nov. 23, 2007, 4 pages total.

(Continued)

*Primary Examiner* — Melanie Hand
(74) *Attorney, Agent, or Firm* — Kilpatrick Townsend & Stockton LLP

(57) ABSTRACT

The present invention generally provides improved medical devices, systems, and methods. Embodiments may be particularly well suited for the treatment of dermatological and/or cosmetic defects, and alternative embodiments may be configured for treatment of a wide range of target tissues. Some embodiments of the present invention apply cooling with at least one small, tissue-penetrating probe, the probe often comprising a needle having a size suitable for inserting through an exposed surface of the skin of a patient without leaving a visible scar. The cooling may remodel one or more target tissue so as to effect a desired change in a composition of the target tissue and/or a change in its behavior. Exemplary embodiments make use of replaceable needle probes supported by a probe body handle, with small needle probes often being replaced during treatment of a single patient. Unlike the large format cryogenic cooling systems of the past, small cryogenic cooling needle probes may dull or be damaged by insertion. Careful control over the control of cryogenic cooling fluid into a needle probe can allow the length of the active cooling to be controlled through depletion of liquid from an evaporating cryogenic cooling flow. Hence, even needles having similar external structures may provide differing lengths of an iceball along the needle axis. Surprisingly, small cryogenic cooling needles and/or other cryogenic cooling probes having a lubricious coating will allow safe removal of the probe from the treatment region while at least a portion of the tissue remains frozen, significantly decreasing the overall time for a procedure involving many insertion/freeze/removal cycles.

14 Claims, 17 Drawing Sheets

U.S. PATENT DOCUMENTS

| | | | |
|---|---|---|---|
| 3,507,283 A | 4/1970 | Thomas, Jr. | |
| 3,532,094 A | 10/1970 | Stahl | |
| 3,664,344 A | 5/1972 | Bryne | |
| 3,795,245 A | 3/1974 | Allen, Jr. et al. | |
| 3,830,239 A | 8/1974 | Stumpf et al. | |
| 3,886,945 A | 6/1975 | Stumpf et al. | |
| 3,889,681 A | 6/1975 | Waller et al. | |
| 3,951,152 A | 4/1976 | Crandell et al. | |
| 3,993,075 A | 11/1976 | Lisenbee et al. | |
| 4,140,109 A | 2/1979 | Savic et al. | |
| 4,207,897 A | 6/1980 | Lloyd et al. | |
| 4,306,568 A | 12/1981 | Torre | |
| 4,376,376 A | 3/1983 | Gregory | |
| 4,404,862 A | 9/1983 | Harris, Sr. | |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,200,170 A | 4/1993 | McDow | |
| 5,334,181 A | 8/1994 | Rubinsky et al. | |
| 5,571,147 A | 11/1996 | Sluijter et al. | |
| 5,647,868 A | 7/1997 | Chinn | |
| 5,755,753 A | 5/1998 | Knowlton | |
| 5,814,040 A | 9/1998 | Nelson et al. | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A | 3/2000 | Rubinsky | |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,182,666 B1 | 2/2001 | Dobak, III | |
| 6,196,839 B1 | 3/2001 | Ross | |
| 6,277,099 B1 | 8/2001 | Strowe et al. | |
| 6,277,116 B1 | 8/2001 | Utely et al. | |
| 6,432,102 B2 | 8/2002 | Joye et al. | |
| 6,494,844 B1 | 12/2002 | Van Bladel et al. | |
| 6,503,246 B1 | 1/2003 | Har-Shai et al. | |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,648,880 B2 | 11/2003 | Chauvet et al. | |
| 6,669,688 B2 | 12/2003 | Svaasand et al. | |
| 6,672,095 B1 | 1/2004 | Luo | |
| 6,706,037 B2 | 3/2004 | Zvuloni et al. | |
| 6,723,092 B2 | 4/2004 | Brown et al. | |
| 6,749,624 B2 | 6/2004 | Knowlton | |
| 6,761,715 B2 | 7/2004 | Carroll | |
| 6,764,493 B1 | 7/2004 | Weber et al. | |
| 6,786,902 B1 | 9/2004 | Rabin et al. | |
| 6,789,545 B2 | 9/2004 | Littrup et al. | |
| 6,840,935 B2 * | 1/2005 | Lee | 606/34 |
| 6,858,025 B2 | 2/2005 | Maurice | |
| 6,905,492 B2 | 6/2005 | Zvuloni et al. | |
| 6,960,208 B2 | 11/2005 | Bourne et al. | |
| 7,001,400 B1 | 2/2006 | Modesitt et al. | |
| 7,081,111 B2 | 7/2006 | Svaasand et al. | |
| 7,083,612 B2 | 8/2006 | Littrup et al. | |
| 7,195,616 B2 | 3/2007 | Diller et al. | |
| 7,311,672 B2 | 12/2007 | Van Bladel et al. | |
| 7,367,341 B2 | 5/2008 | Anderson et al. | |
| 7,402,140 B2 | 7/2008 | Spero et al. | |
| 7,422,586 B2 | 9/2008 | Morris et al. | |
| 2002/0013602 A1 | 1/2002 | Huttner | |
| 2002/0068929 A1 | 6/2002 | Zvuloni | |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0181896 A1 | 9/2003 | Zvuloni et al. | |
| 2004/0122482 A1 | 6/2004 | Tung et al. | |
| 2004/0162551 A1 | 8/2004 | Brown et al. | |
| 2004/0167505 A1 | 8/2004 | Joye et al. | |
| 2004/0191229 A1 | 9/2004 | Link et al. | |
| 2004/0204705 A1 | 10/2004 | Lafontaine | |
| 2004/0210212 A1 | 10/2004 | Maurice | |
| 2004/0215178 A1 | 10/2004 | Maurice | |
| 2004/0215294 A1 | 10/2004 | Littrup et al. | |
| 2004/0225276 A1* | 11/2004 | Burgess | 604/506 |
| 2004/0243116 A1 | 12/2004 | Joye et al. | |
| 2005/0177147 A1 | 8/2005 | Vancelette et al. | |
| 2005/0177148 A1 | 8/2005 | van der Walt et al. | |
| 2005/0203505 A1 | 9/2005 | Megerman et al. | |
| 2005/0203593 A1 | 9/2005 | Shanks et al. | |
| 2005/0209565 A1 | 9/2005 | Yuzhakov et al. | |
| 2005/0209587 A1 | 9/2005 | Joye et al. | |
| 2005/0228288 A1* | 10/2005 | Hurst | 600/459 |
| 2005/0251103 A1 | 11/2005 | Steffen et al. | |
| 2005/0261753 A1 | 11/2005 | Littrup et al. | |
| 2005/0276759 A1 | 12/2005 | Roser et al. | |
| 2005/0283148 A1 | 12/2005 | Janssen et al. | |
| 2006/0009712 A1 | 1/2006 | Van Bladel et al. | |
| 2006/0015092 A1 | 1/2006 | Joye et al. | |
| 2006/0069385 A1 | 3/2006 | Lafontaine et al. | |
| 2006/0079914 A1 | 4/2006 | Modesitt et al. | |
| 2006/0084962 A1 | 4/2006 | Joye et al. | |
| 2006/0111732 A1 | 5/2006 | Gibbens et al. | |
| 2006/0129142 A1 | 6/2006 | Reynolds | |
| 2006/0142785 A1 | 6/2006 | Modesitt et al. | |
| 2006/0173469 A1 | 8/2006 | Klein et al. | |
| 2006/0189968 A1 | 8/2006 | Howlett et al. | |
| 2006/0190035 A1 | 8/2006 | Hushka et al. | |
| 2006/0200117 A1 | 9/2006 | Hermans | |
| 2006/0212028 A1 | 9/2006 | Joye et al. | |
| 2006/0212048 A1 | 9/2006 | Crainich | |
| 2006/0223052 A1 | 10/2006 | MacDonald et al. | |
| 2007/0060921 A1 | 3/2007 | Janssen et al. | |
| 2007/0088217 A1 | 4/2007 | Babaev | |
| 2007/0129714 A1 | 6/2007 | Elkins et al. | |
| 2007/0156125 A1 | 7/2007 | DeLonzor | |
| 2007/0161975 A1 | 7/2007 | Goulko | |
| 2007/0167943 A1 | 7/2007 | Janssen et al. | |
| 2007/0167959 A1 | 7/2007 | Modesitt et al. | |
| 2007/0179509 A1 | 8/2007 | Nagata et al. | |
| 2007/0198071 A1 | 8/2007 | Ting et al. | |
| 2007/0255362 A1 | 11/2007 | Levinson et al. | |
| 2007/0270925 A1 | 11/2007 | Levinson | |
| 2008/0077201 A1 | 3/2008 | Levinson et al. | |
| 2008/0077202 A1 | 3/2008 | Levinson | |
| 2008/0077211 A1 | 3/2008 | Levinson et al. | |
| 2008/0154254 A1 | 6/2008 | Burger et al. | |
| 2008/0183164 A1 | 7/2008 | Elkins et al. | |
| 2008/0287839 A1 | 11/2008 | Rosen et al. | |
| 2009/0018623 A1 | 1/2009 | Levinson et al. | |
| 2009/0018624 A1 | 1/2009 | Levinson et al. | |
| 2009/0018625 A1 | 1/2009 | Levinson et al. | |
| 2009/0018626 A1 | 1/2009 | Levinson et al. | |
| 2009/0018627 A1 | 1/2009 | Levinson et al. | |
| 2009/0171334 A1 | 7/2009 | Elkins et al. | |
| 2009/0248001 A1 | 10/2009 | Burger et al. | |

FOREIGN PATENT DOCUMENTS

| | | |
|---|---|---|
| EP | 0 777123 A2 | 6/1997 |
| EP | 1 074 273 A1 | 2/2001 |
| EP | 1377327 B1 | 9/2007 |
| EP | 1 862 125 | 12/2007 |
| GB | 1 360 353 A | 7/1974 |
| GB | 1402632 | 8/1975 |
| JP | 10-014656 | 1/1998 |
| JP | 2006-130055 | 5/2006 |
| RU | 2254060 | 6/2005 |
| WO | WO 97/49344 | 12/1997 |
| WO | WO 01/97702 | 12/2001 |
| WO | WO 02/092153 | 11/2002 |
| WO | WO 2004/039440 A1 | 5/2004 |
| WO | WO 2004/045434 | 6/2004 |
| WO | WO 2004/089460 | 10/2004 |
| WO | WO 2005/000106 | 1/2005 |
| WO | WO 2005/079321 A2 | 9/2005 |
| WO | WO 2006/012128 | 2/2006 |
| WO | WO 2006/023348 | 3/2006 |
| WO | WO 2006/125835 | 11/2006 |
| WO | WO 2007/037326 | 4/2007 |
| WO | WO 2007/089603 | 8/2007 |

| | | |
|---|---|---|
| WO | WO 2007/129121 | 11/2007 |
| WO | WO 2007/135629 | 11/2007 |
| WO | WO 2009/026471 | 2/2009 |

OTHER PUBLICATIONS

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

One Med Group, LLC., [webpage] "CryoProbe™", retrieved from the Internet: <<http://www.onemedgroup.com/>> on Feb. 8, 2008, 2 pages total.

Cryosurgical Concepts, Inc., [webpage] "CryoProbe™", retrieved from the Internet: << http://www.cryo-surgical.com//>> on Feb. 8, 2008, 2 pages total.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

Advanced Cosmetic Intervention, Inc. [webpage], retrieved from the Internet: <<http://www.acisurgery.com>>, copyright 2007, 1 page.

U.S. Appl. No. 11/614,887, filed Dec. 21, 2006; first named inventor: Keith Burger.

U.S. Appl. No. 11/770,185, filed Jun. 28, 2007; first named inventor: Lisa Elkins.

Utley et al., "Radiofrequency Ablation of the Nerve to the Corrugator Muscle for the Elimination of Glabellar Furrowing," Arch. Facial Plastic Surgery 1: 46-48, 1999.

Har-Shai et al., "Effect of skin surface temperature on skin pigmentation during contact and intralesional cryosurgery of hypertrophic scars and Kleoids," Journal of the European Academy of Dermatology and Venereology 21 (2):191-198.

Magalov et al., "Isothermal volume contours generated in a freezing gel by embedded cryo-needles with applications to cryo-surgery," Cryobiology, Oct. 2007; 55(2):127-137.

Rewcastle et al., "A model for the time dependent three-dimensional thermal distribution within iceballs surrounding multiple cryoprobes," Med Phys. Jun. 2001;28(6):1125-1137.

International Search Report of PCT Application PCT/US07/87893, dated Jun. 18, 2008, 14 pages total.

Yang et al., "Apoptosis induced by cryo-injury in human colorectal cancer cells is associated with mitochondrial dysfunction.," Int J Cancer. Jan. 20, 2003;103(3):360-369.

Dasiou-Plankida, "Fat injections for facial rejuvenation: 17 years experience in 1720 patients," Journal of Cosmetic Dermatology, Oct. 22, 2004; 2(3-4): 119-125.

International Search Report and Written Opinion of PCT Application No. PCT/US08/53876, dated Aug. 15, 2008, 16 pages total.

* cited by examiner

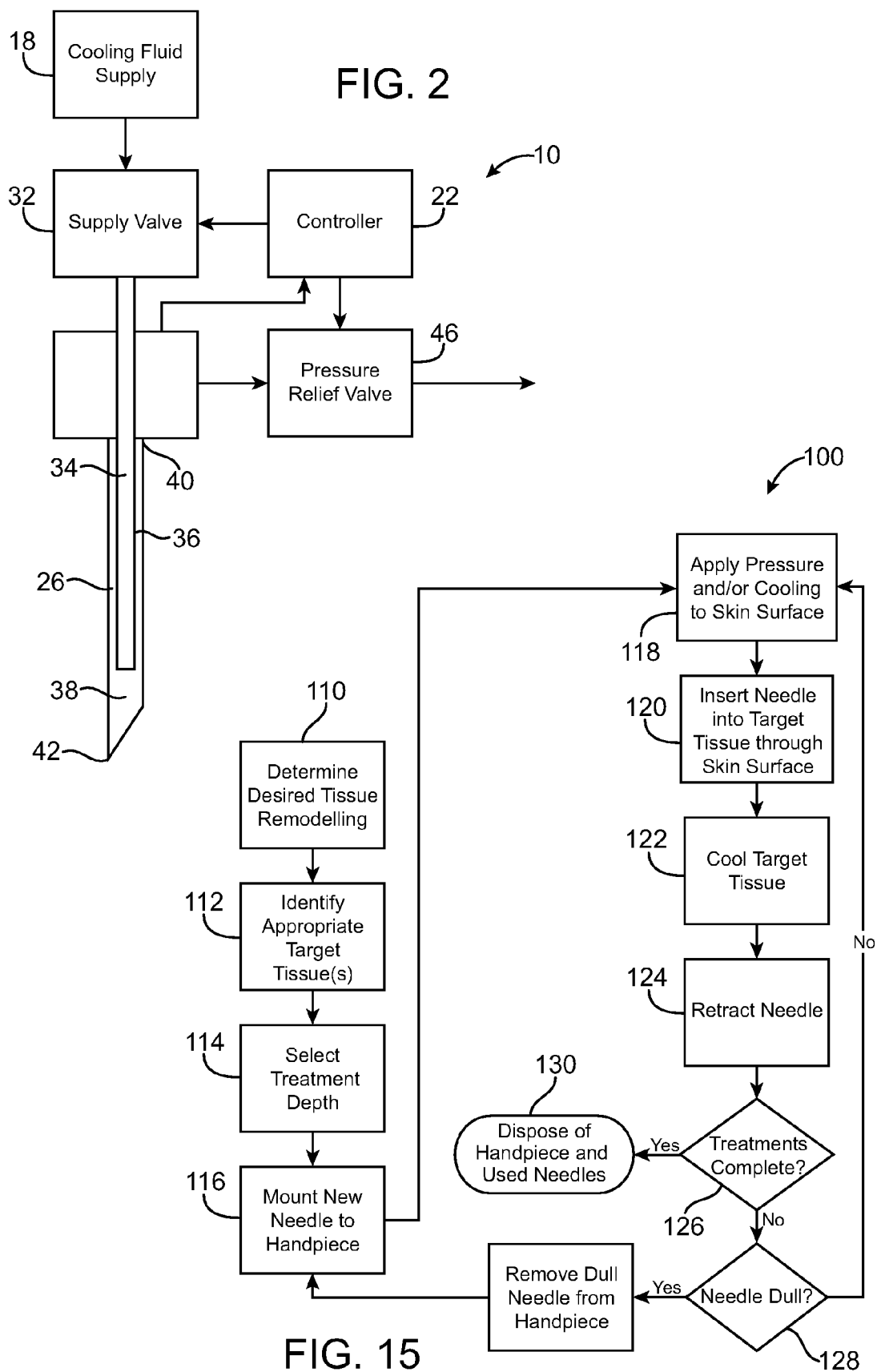

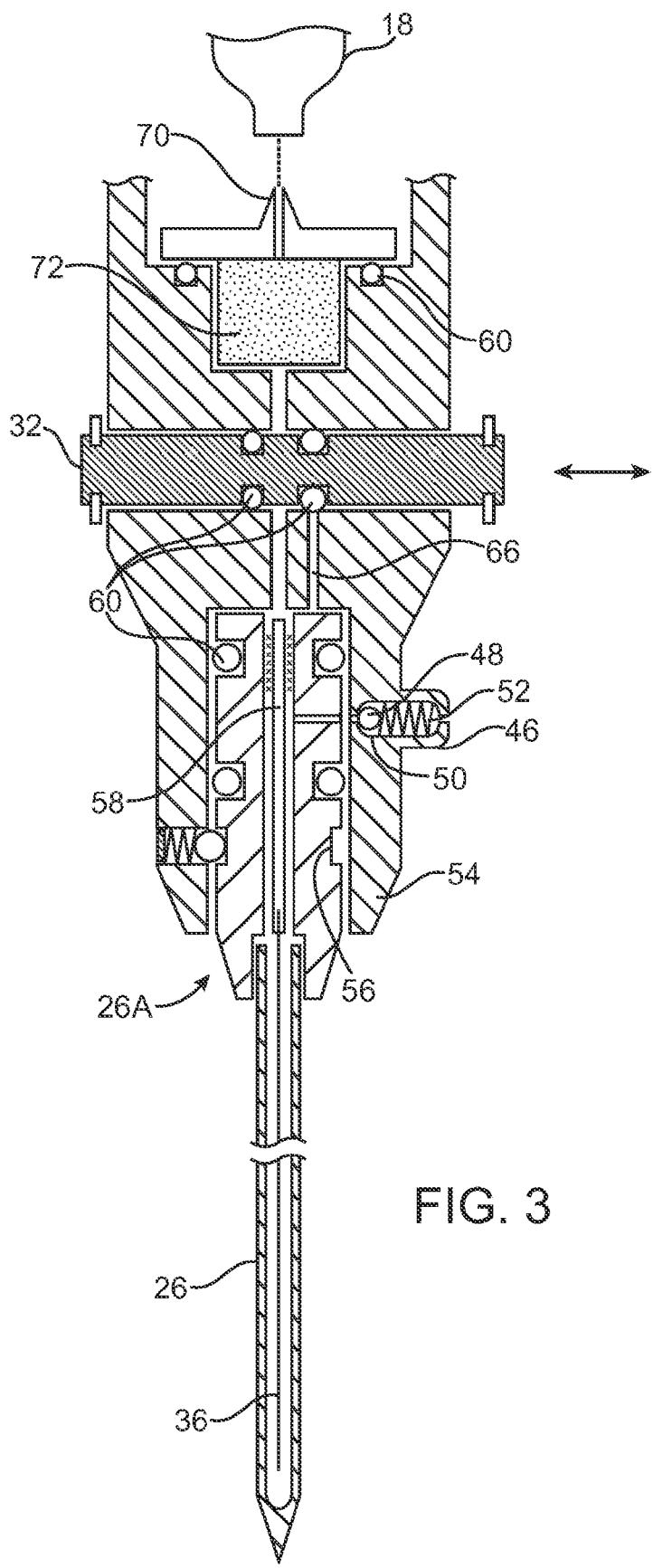

Section AA

Section BB

REPLACEABLE AND/OR EASILY REMOVABLE NEEDLE SYSTEMS FOR DERMAL AND TRANSDERMAL CRYOGENIC REMODELING

CROSS-REFERENCES TO RELATED APPLICATIONS

Not applicable

STATEMENT AS TO RIGHTS TO INVENTIONS MADE UNDER FEDERALLY SPONSORED RESEARCH AND DEVELOPMENT

Not applicable

REFERENCE TO A "SEQUENCE LISTING," A TABLE, OR A COMPUTER PROGRAM LISTING APPENDIX SUBMITTED ON A COMPACT DISK

Not applicable

BACKGROUND OF THE INVENTION

The present invention is generally directed to medical devices, systems, and methods, particularly for cooling-induced remodeling of tissues. Embodiments of the invention include devices, systems, and methods for applying cryogenic cooling to dermatological tissues so as to selectively remodel one or more target tissues along and/or below an exposed surface of the skin. Embodiments may be employed for a variety of cosmetic conditions, optionally by inhibiting undesirable and/or unsightly effects on the skin (such as lines, wrinkles, or cellulite dimples) or on other surrounding tissue. Other embodiments may find use for a wide range of medical indications. The remodeling of the target tissue may achieve a desired change in its behavior or composition.

The desire to reshape various features of the human body to either correct a deformity or merely to enhance one's appearance is common. This is evidenced by the growing volume of cosmetic surgery procedures that are performed annually.

Many procedures are intended to change the surface appearance of the skin by reducing lines and wrinkles. Some of these procedures involve injecting fillers or stimulating collagen production. More recently, pharmacologically based therapies for wrinkle alleviation and other cosmetic applications have gained in popularity.

Botulinum toxin type A (BOTOX®) is an example of a pharmacologically based therapy used for cosmetic applications. It is typically injected into the facial muscles to block muscle contraction, resulting in temporary enervation or paralysis of the muscle. Once the muscle is disabled, the movement contributing to the formation of the undesirable wrinkle is temporarily eliminated. Another example of pharmaceutical cosmetic treatment is mesotherapy, where a cocktail of homeopathic medication, vitamins, and/or drugs approved for other indications is injected into the skin to deliver healing or corrective treatment to a specific area of the body. Various cocktails are intended to effect body sculpting and cellulite reduction by dissolving adipose tissue, or skin resurfacing via collagen enhancement. Development of non-pharmacologically based cosmetic treatments also continues. For example, endermology is a mechanical based therapy that utilizes vacuum suction to stretch or loosen fibrous connective tissues which are implicated in the dimpled appearance of cellulite.

While BOTOX® and/or mesotherapies may temporarily reduce lines and wrinkles, reduce fat, or provide other cosmetic benefits they are not without their drawbacks, particularly the dangers associated with injection of a known toxic substance into a patient, the potential dangers of injecting unknown and/or untested cocktails, and the like. Additionally, while the effects of endermology are not known to be potentially dangerous, they are brief and only mildly effective.

In light of the above, it would be desirable to provide improved medical devices, systems, and methods, particularly for treatment of wrinkles, fat, cellulite, and other cosmetic defects. It would be particularly desirable if these new techniques provided an alternative visual appearance improvement mechanism which could replace and/or compliment known bioactive and other cosmetic therapies, ideally allowing patients to decrease or eliminate the injection of toxins and harmful cocktails while providing similar or improved cosmetic results. It would also be desirable if such techniques were performed percutaneously using only local or no anesthetic with minimal or no cutting of the skin, no need for suturing or other closure methods, no extensive bandaging, and limited or no bruising or other factors contributing to extended recovery or patient "down time". It would further be desirable to provide new devices, systems, and methods for treatment of other cosmetic and/or dermatological conditions (and potentially other target tissues), particularly where the treatments may be provided with greater accuracy and control, less collateral tissue injury and/or pain, and greater ease of use.

BRIEF SUMMARY OF THE INVENTION

The present invention generally provides improved medical devices, systems, and methods. Embodiments may be particularly well suited for the treatment of dermatological and/or cosmetic defects, and alternative embodiments may be configured for treatment of a wide range of target tissues. Some embodiments of the present invention apply cooling with at least one small, tissue-penetrating probe, the probe often comprising a needle having a size suitable for inserting through an exposed surface of the skin of a patient without leaving a visible scar. The cooling may remodel one or more target tissue so as to effect a desired change in a composition of the target tissue and/or a change in its behavior. Unlike the large format cryogenic cooling systems of the past, small cryogenic cooling needle probes may dull or be damaged by insertion. Exemplary embodiments make use of replaceable needle probes supported by a probe body handle, with small needle probes often being replaced during treatment of a single patient. Careful control over the cryogenic cooling fluid introduced into a needle probe can allow the length of the active cooling to be controlled through depletion of evaporating cryogenic cooling liquid. Hence, even needles having similar external structures may provide differing lengths of effective remodeling along the needle axis. Surprisingly, small cryogenic cooling needles and/or other cryogenic cooling probes having a lubricious coating will allow safe removal of the probe from the treatment region while at least a portion of the tissue remains frozen, significantly decreasing the overall time for a procedure involving many insertion/freeze/removal cycles.

In a first aspect, the invention provides a method for treating tissue of a patient. The method comprises inserting a first needle through a first insertion point and into a first target region of the tissue by manipulating handle. The handle supports the first needle via a needle interface. The first target region is cooled with the first needle and the first needle is removed from the patient. The first needle is replaced in the needle interface with a second needle. The second needle is inserted through the second insertion point and into a second target region of the tissue by manipulating the handle. The second target region is cooled with the second needle.

The second needle may optionally have size and/or cooling characteristics which are similar to those of the first needle. Such needle replacement may be particularly useful when using small needles that can become dull after a limited number of insertions into the patient. In other embodiments, the second needle may have size and/or cooling characteristics that differ from those of the first needle, such as having a different length, needle gauge size or diameter, active cooling length, or the like. In some embodiments, the first needle may be included in a first needle assembly that has only a single needle, while the second needle is included in a needle assembly having a plurality of needles. The needles of the second needle assembly may be simultaneously inserted into the target tissue, with the needles often being substantially parallel. A cooling fluid supply tube (and its associated lumen) may extend from a common cooling fluid supply of the needle interface, and cooling fluid vaporization lumens of each needle may flow to a common pressure-regulated exhaust path, also often via the needle interface. In many embodiments, cooling with the plurality of needles of the second needle assembly may be performed so that the cooled tissues are remodeled throughout a contiguous treatment zone. In other embodiments, the needle spacing and the like may result in a plurality of discrete remodeled zones.

Typically, the first and second needles will each have a sharpened distal tip and a 20-gauge needle size or less. The needles may be disposed of after use to avoid inserting a dull needle into the patient, with the needles optionally being inserted a single time, or alternatively being inserted a plurality of times (often less than ten times, and in many cases, less than five times) through the patient's skin. The handle of the system may be included in a probe body, and a fluid supply cartridge and battery may be supported and/or housed by the probe body. The probe body may be disposed of so that one or all of these components are used to treat only a single patient. Such a structure also helps avoid any requirement for a tether, power port, flexible supply line, or the like, which might otherwise inhibit manipulation and use of the hand-held probe. Cooling will often be terminated by closing a cooling fluid shutoff valve disposed along a cooling fluid supply path between a cooling fluid source and the lumen. As cooling may be performed by evaporating liquid cooling fluid within a lumen of the needle, a volume of the supply path between the valve and the lumen will preferably be quite low (typically being less than 0.05 cubic inches, optionally being less than 0.005 cubic inches) so as to allow more accurate control of the treatment time. The supply path between the valve and the needle lumen is preferably vented when the valve is closed so as to avoid continuing cooling by any residual cryogenic liquid within that volume.

In another aspect, the invention provides a method for treating a target tissue of a patient. The method comprises inserting a cooling probe distally through a collateral tissue and into the target tissue. The cooling probe has a lumen with a distal portion adjacent the target tissue and a proximal portion adjacent the collateral tissue. Cooling fluid is introduced into the distal portion of the lumen, and evaporation of liquid from the cooling fluid into gas occurs as the cooling fluid flows proximally within the distal portion of the lumen. This evaporation occurs so that the evaporation cools the target tissue sufficiently for the desired remodeling treatment. Additionally, the evaporation occurs so that the liquid is depleted from the cooling fluid sufficiently when the gas passes through the proximal portion of the lumen to inhibit cooling of the collateral tissue.

The target tissue along the distal portion of the lumen can be cooled to a treatment temperature which is in a first temperature range. The collateral tissue along the proximal portion of the lumen will typically be cooled to a collateral tissue temperature in a second temperature range that is warmer than the first temperature range. Note that the differential in cooling effects between the distal and proximal lumen portions may occur despite the structure of the needle having a substantially uniform and/or consistent cross-section along the proximal and distal portions. Advantageously, a length of the distal, tissue remodeling portion may be selected from among a plurality of alternative lengths by selecting the probe for mounting to a probe body. Alternative probes may include differing cooling fluid supply paths so as to introduce differing cooling fluid supply flows with corresponding differing liquid depletion characteristics. More specifically, using otherwise similar probe structures having differing cooling fluid supply tubes with differing inner diameters and/or differing lengths may effectively vary the axial length of tissue that is remodeled, particularly where a significant portion of the metering of the cooling fluid flow is effected by the flow resistance of the cooling fluid supply lumen. Advantageously, the treatment temperatures along the distal portion may remain substantially uniform so long as there continues to be a sufficient mixture of cooling liquid and evaporated gas in the cooling fluid flow. As the cooling fluid liquid is depleted from that flow, temperatures of the flow may increase and/or the heat transfer from the surrounding probe structure (and tissue) may significantly decrease, with the change in cooling during a relatively short and predictable axial length of the probe.

In another aspect, the invention provides a method for remodeling a target tissue of a patient. The method comprises inserting a cooling probe distally into the target tissue. The target tissue is cooled sufficiently to freeze a region of the target tissue. The cooling probe is removed from the target tissue while the region remains frozen.

In many embodiments, the cooling probe may be removed less than 15 seconds after the termination of cooling, with the probe typically being removed less than 10 seconds after the cooling (or even less than 5 seconds after the cooling). Such counterintuitive removal of a cryogenic cooling probe from a still-frozen treatment region may be safely performed, for example, where the cooling is effected using a cooling probe having a cross-sectional size of a 20-gauge needle or less, the needle often being 25 gauge or less, and ideally being 30 gauge. A melted zone may be relatively quickly formed between such a probe and the surrounding frozen tissue to facilitate safe removal of the probe, despite the region remaining frozen. Hence, not all of the initially-frozen tissue may remain frozen during removal, although the majority of the tissue that has been frozen may remain frozen in many embodiments.

Many embodiments of the present invention may facilitate removal of a cryogenic treatment probe from a still-frozen tissue region by cooling the target tissue through a lubricious coating of the probe. Although the lubricious coating will often have a thermal conductivity which is significantly lower than that of the underlying probe material (the probe material typically comprising stainless steel hypotube or the like for small needle probes), the total thermal transfer from the target tissue can be facilitated by using a lubricious coating having a thickness which is significantly less than that of the probe material. Additionally, the internal temperature of a cryogenic fluid vaporization chamber or lumen may be selected to generate the desired cooling characteristics despite the thermal insulation of the lubricious coating. Nonetheless, overall treatment times will be significantly shorter, particularly where a large number of insertion/cooling/removal cycles are employed, and/or where the total cooling time is relatively short compared to the time for a total thaw of the frozen tissue.

In another aspect, the invention provides a system for treating tissue of a patient. The system comprises a first needle having a proximal end, a distal tissue-penetrating end, a lumen therebetween, and a cooling fluid supply lumen extending distally to a port within the needle lumen. The needle has a size of a 20-gauge needle or less. A second needle has a proximal end, a distal tissue-penetrating end and a lumen therebetween. A cooling fluid supply lumen extends distally to a port within the lumen of the second needle, the needle also having a size of a 20-gauge needle or less. A probe body has a handle supporting a cooling fluid source and a needle interface for sequentially receiving the first and second needles. Vaporization within the lumen of the received needle cools the tissue when the needle is inserted therein and cooling fluid is introduced from the cooling fluid supply through the port.

In another aspect, the invention provides a system for treatment of the target tissue of a patient. The patient has a collateral tissue adjacent the target tissue, and the system comprises a probe having a proximal end and a distal end. The distal end is insertable through the collateral tissue and into the target tissue. The inserted probe has a lumen with a proximal portion adjacent the target tissue and a distal portion adjacent the collateral tissue when the distal end is inserted. A cooling fluid source is in fluid communication with the distal portion of the lumen. The source is configured so that, when cooling fluid flows from the source into (and proximally along) the lumen of the inserted probe, liquid of the cooling fluid evaporates into gas within the distal portion of the lumen such that the evaporation cools the target tissue sufficiently for the treatment. Additionally, the liquid is depleted sufficiently when the cooling fluid passes through the proximal portion of the lumen to inhibit cooling of the collateral tissue.

In yet another aspect, the invention provides a system for remodeling a target tissue of the patient. The system comprises a cooling probe insertable distally into the target tissue. The cooling probe has a cooling surface for cooling the target tissue sufficiently to freeze a region of the target tissue. A lubricious coating is disposed over the cooling surface of the probe to facilitate removing the cooling probe from the target tissue while the region remains frozen.

Exemplary lubricious and/or hydrophobic coatings include polymers, such as a PTFE Teflon™ polymers, a silicone, or the like. Typical thicknesses of the coating may be from about 0.00005 inches to about 0.001 inches, with an exemplary PTFE polymer coating having a thickness of about 0.0005 inches and exemplary silicone coatings being thinner. In some embodiments, a portion of the probe (such as a distal end or small region near the distal end) may be free of the coating so as to allow use of the coating-free region as an electrode or the like.

BRIEF DESCRIPTION OF THE DRAWINGS

FIG. 2 schematically illustrates components that may be included in the treatment system.

FIG. 3 is a schematic cross-sectional view of an embodiment of a distal portion of the probe and system of FIG. 1B, showing a replaceable needle and an pressure relief valve with a limited exhaust volume.

FIG. 3A illustrates an exemplary fused silica cooling fluid supply tube for use in the replaceable needle of FIG. 3.

FIG. 15 is a flow chart schematically illustrating a method for treatment using the disposable cryogenic probe and system of FIG. 1B.

DETAILED DESCRIPTION OF THE INVENTION

The present invention provides improved medical devices, system, and methods. Embodiments of the invention will facilitate remodeling of tissues disposed at and below the skin, optionally to treat a cosmetic defect, a lesion, a disease state, and/or so as to alter a shape of the overlying skin surface.

Among the most immediate applications of the present invention may be the amelioration of lines and wrinkles, particularly by inhibiting muscular contractions which are associated with these cosmetic defects so as so improve an appearance of the patient. Rather than relying entirely on a pharmacological toxin or the like to disable muscles so as to induce temporary paralysis, many embodiments of the invention will at least in part employ cold to immobilize muscles. Advantageously, nerves, muscles, and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a permanent treatment that limits or avoids inflammation and mobilization of skeletal muscle satellite repair cells. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling for treatment of cosmetic and other defects may be found in co-pending U.S. patent application Ser. No. 11/295,204, filed on Dec. 5, 2005 and entitled "Subdermal Cryogenic Remodeling of Muscle, Nerves, Connective Tissue, and/or Adipose Tissue (Fat)," the full disclosure of which is incorporated herein by reference.

In addition to cosmetic treatments of lines, wrinkles, and the like, embodiments of the invention may also find applications for treatments of subdermal adipose tissues, benign, pre-malignant lesions, malignant lesions, acne and a wide range of other dermatological conditions (including dermatological conditions for which cryogenic treatments have been proposed and additional dermatological conditions), and the like. Embodiments of the invention may also find applications for alleviation of pain, including those associated with muscle spasms. Hence, a variety of embodiments may be provided.

Figure 1A:
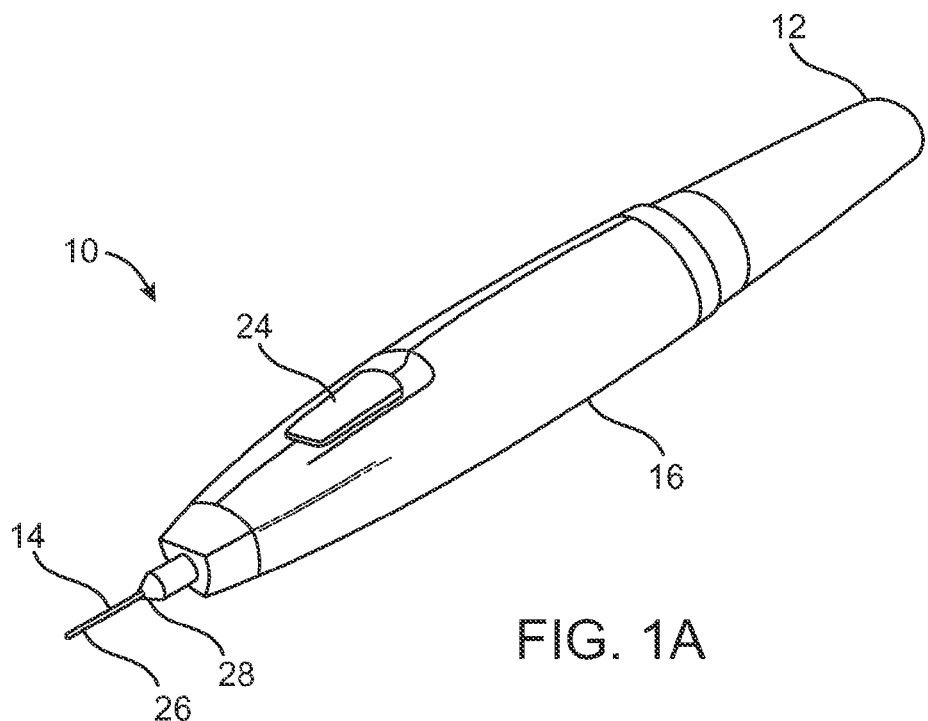
FIG. 1A is a perspective view of a self-contained subdermal cryogenic remodeling probe and system, according to an embodiment of the invention.
Figure 1B:
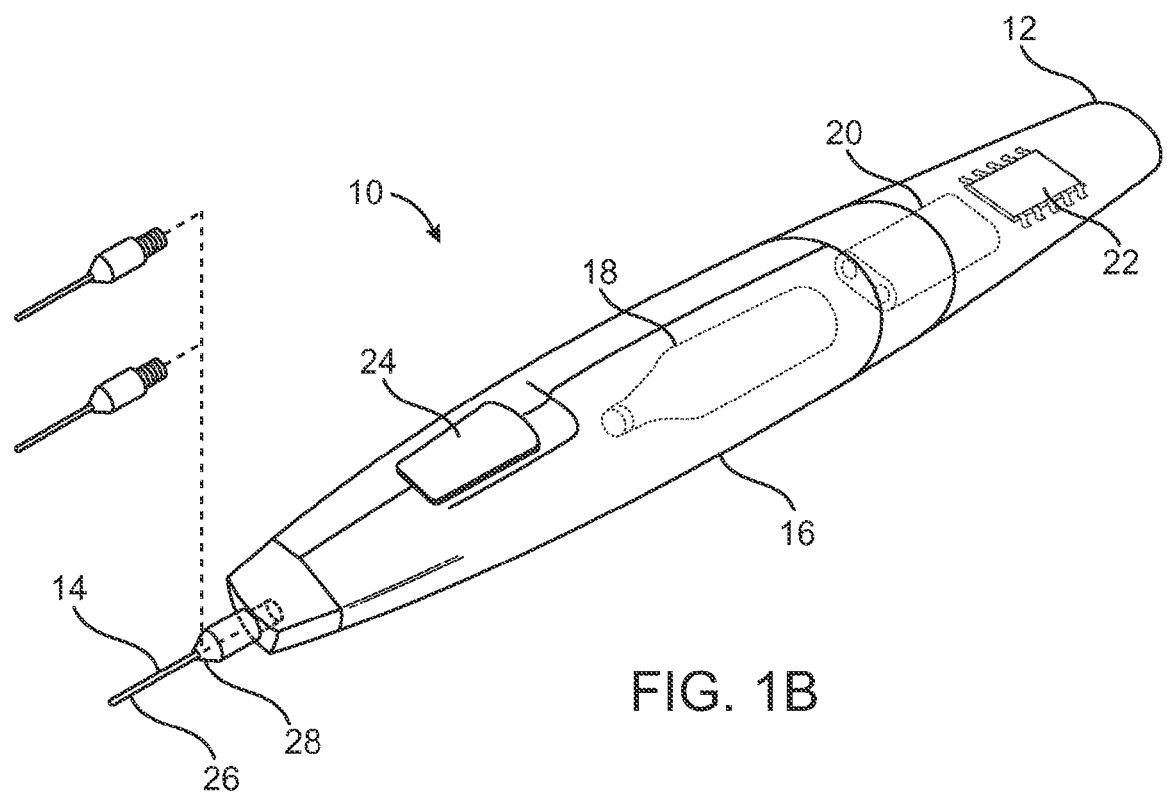
FIG. 1B is a partially transparent perspective view of the self-contained probe of FIG. 1A, showing internal components of the cryogenic remodeling system and schematically illustrating replacement treatment needles for use with the disposable probe.

Referring now to FIGS. 1A and 1B, a system for cryogenic remodeling here comprises a self-contained probe handpiece generally having a proximal end 12 and a distal end 14. A handpiece body or housing 16 has a size and shape suitable for supporting in a hand of a surgeon or other system operator. As can be seen most clearly in FIG. 1B, a cryogenic cooling fluid supply 18 and electrical power source 20 are found within housing 16, along with a circuit 22 having a processor for controlling cooling applied by self-contained system 10 in response to actuation of an input 24. Some embodiments may, at least in part, be manually activated, such as through the use of a manual supply valve and/or the like, so that processors, electrical power supplies, and the like may be absent.

Extending distally from distal end 14 of housing 16 is a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 comprises a 30 g needle having a sharpened distal end that is axially sealed. Probe 26 may have an axial length between distal end 14 of housing 16 and the distal end of the needle of between about ½ mm and 5 cm, preferably having a length from about 1 cm to about 3 cm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 will comprise a 16 g or smaller size needle, often comprising a 20 g needle or smaller, typically comprising a 25 g or smaller needle.

Addressing some of the components within housing 16, the exemplary cooling fluid supply 18 comprises a cartridge containing a liquid under pressure, with the liquid preferably having a boiling temperature of the less than 37° C. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A valve (not shown) may be disposed along the cooling fluid flow path between cartridge 18 and probe 26, or along the cooling fluid path after the probe so as to limit the temperature, time, rate of temperature change, or other cooling characteristics. The valve will often be powered electrically via power source 20, per the direction of processor 22, but may at least in part be manually powered. The exemplary power source 20 comprises a rechargeable or single-use battery.

The exemplary cooling fluid supply 18 comprises a single-use cartridge. Advantageously, the cartridge and cooling fluid therein may be stored and/or used at (or even above) room temperature. The cartridges may have a frangible seal or may be refillable, with the exemplary cartridge containing liquid $N_2O$. A variety of alternative cooling fluids might also be used, with exemplary cooling fluids including fluorocarbon refrigerants and/or carbon dioxide. The quantity of cooling fluid contained by cartridge 18 will typically be sufficient to treat at least a significant region of a patient, but will often be less than sufficient to treat two or more patients. An exemplary liquid $N_2O$ cartridge might contain, for example, a quantity in a range from about 7 g to about 30 g of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Referring now to FIG. 2, the flow of cryogenic cooling fluid from fluid supply 18 is controlled by a supply valve 32. Supply valve may comprise an electrically actuated solenoid valve or the like operating in response to control signals from controller 22, and/or may comprise a manual valve. Exemplary supply valves may comprise structures suitable for on/off valve operation, and may provide venting of the cooling fluid path downstream of the valve when cooling flow is halted so as to limit residual cryogenic fluid vaporization and cooling. More complex flow modulating valve structures might also be used in other embodiments.

The cooling fluid from valve 32 flows through a lumen 34 of a cooling fluid supply tube 36. Supply tube 36 is, at least in part, disposed within a lumen 38 of needle 26, with the supply tube extending distally from a proximal end 40 of the needle toward a distal end 42. The exemplary supply tube 36 comprises a fused silica tubular structure 36a having a polymer coating 36b (see FIG. 3A) and extends in cantilever into the needle lumen 38. Supply tube 36 may have an inner lumen with an effective inner diameter 36c of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size 36d of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about ±10 µm or tighter, often being +/−5 µm or tighter, and ideally being +/−3 µm or tighter, as the small diameter supply tube may provide the majority of (or even substantially all of) the metering of the cooling fluid flow into needle 26.

Figure 12:
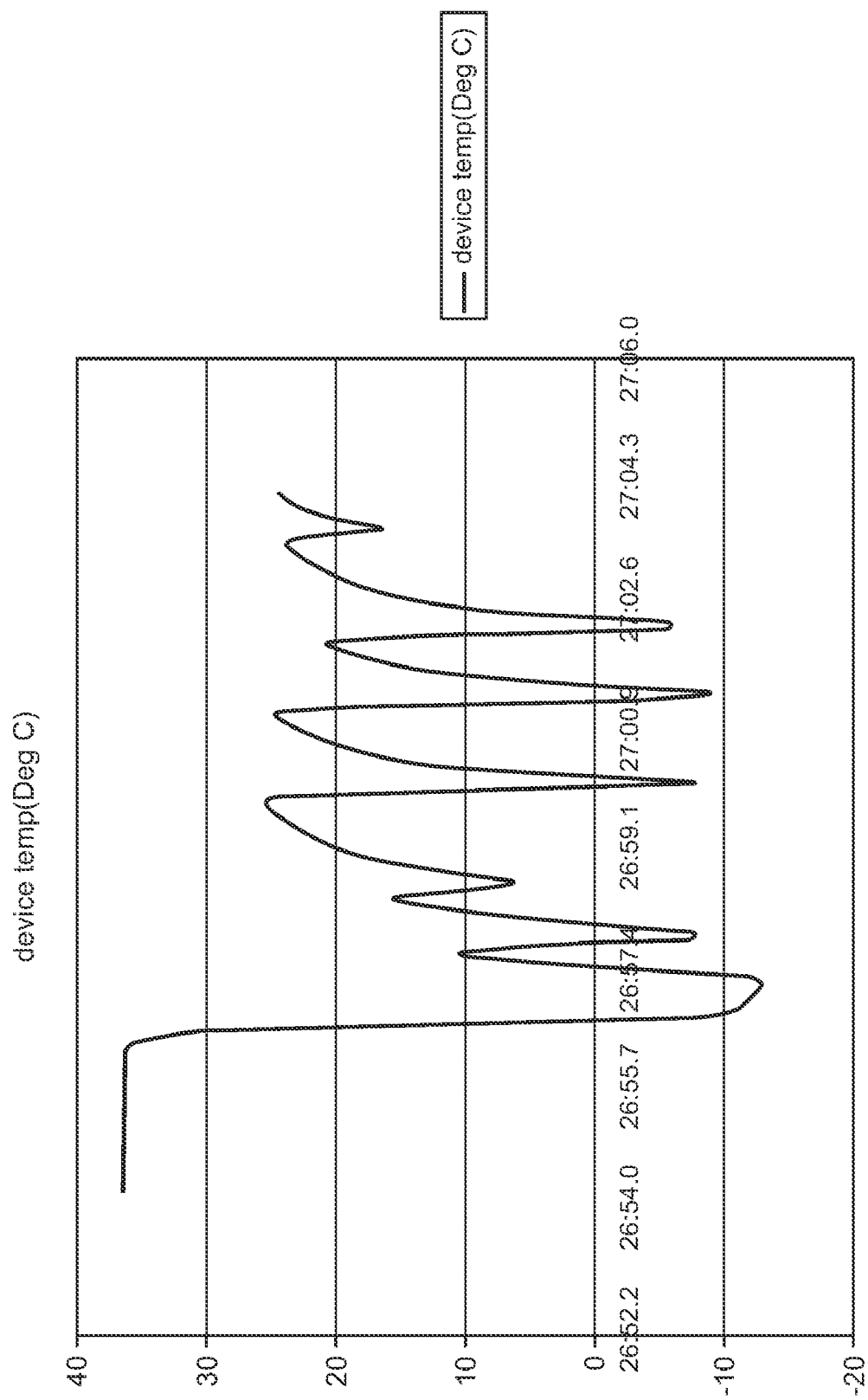
FIG. 12 graphically illustrates non-uniform cooling that can result from inadequate evaporation space within a small cryogenic needle probe.

Though supply tubes 36 having outer jackets of polyimide (or other suitable polymer materials) may bend within the surrounding needle lumen 38, the supply tube should have sufficient strength to avoid collapsing or excessive blow back during injection of cooling fluid into the needle. Polyimide coatings may also provide durability during assembly and use, and the fused silica/polymer structures can handle pressures of up to 100 kpsi. The relatively thin tubing wall and small outer size of the preferred supply tubes allows adequate space for vaporization of the nitrous oxide or other cooling fluid within the annular space between the supply tube 36 and surrounding needle lumen 38. Inadequate space for vaporization might otherwise cause a buildup of liquid in that annular space and inconsistent temperatures, as illustrated in FIG. 12. Exemplary structures for use as supply tube 36 may include the flexible fused silica capillary tubing sold commercially by Polymicro Technologies, LLC of Phoenix, Ariz. under model names TSP, TSG, and TSU, optionally including model numbers TSP 020090, TSP040105, and/or others.

Referring now to FIGS. 2 and 3, the cooling fluid injected into lumen 38 of needle 26 will typically comprises liquid, though some gas may also be injected. At least some of the liquid vaporizes within needle 26, and the enthalpy of vaporization cools the tissue engaged by the needle. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body 48 (here in the form of a ball bearing) urged against a valve seat 50 by a biasing spring 52.

Figure 4:
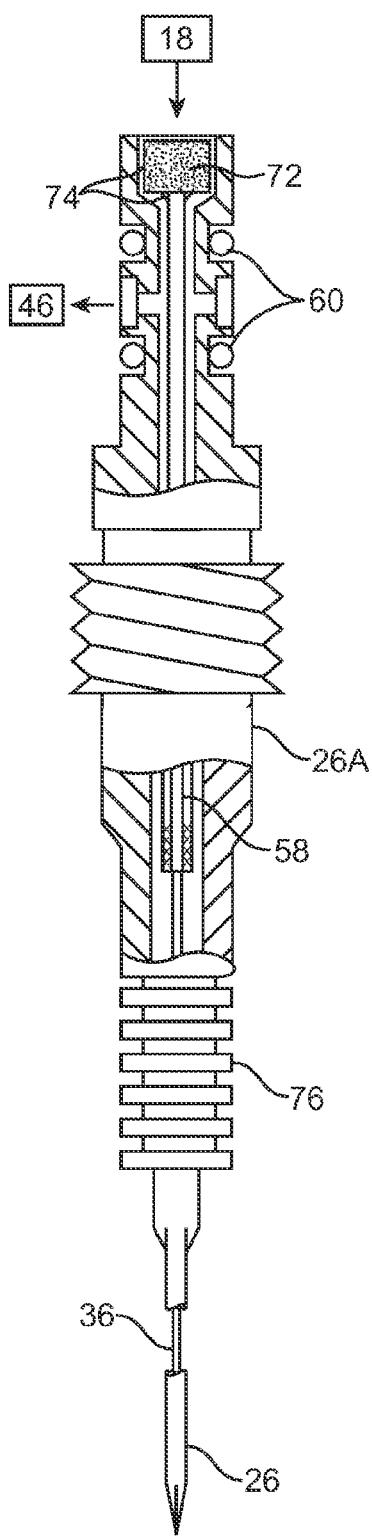
FIG. 4 is a more detailed view of a replaceable needle assembly for use in the system of FIGS. 1A and 1B.

During initiation of a cooling cycle, a large volume along the cooling fluid pathway between the exit from the supply tube and exit from the pressure relief valve 46 may cause excessive transients. In particular, a large volume in this area may result in initial temperatures that are significantly colder than a target and/or steady state temperature, as can be seen in FIG. 13D. This can be problematic, particularly when (for example) the target temperature is only slightly warmer than an undesirable effect inducing temperature, such as when remodeling through apoptosis or the like while seeking to inhibit necrosis. To limit such transients, the pressure relief valve 46 may be integrated into a housing 54 supporting needle 26, with the valve spring 52 being located outside the valve seat (and hence the pressure-control exit from pressure relief valve 46). Additionally, where needle 26 is included in a replaceable needle assembly 26A, pressure relief valve 46 is also located adjacent the interface between the needle assembly and probe handpiece housing 54. A detent 56 may be engaged by a spring supported catch to hold the needle assembly releasably in position, and the components of the needle assembly 26A (such as a brass or other metallic housing, a polyimide tubing 58, needle 26, and the like) may be affixed together using adhesive. Alternatively, as illustrated in FIGS. 1B and 4, the needle assembly and handpiece housing may have corresponding threads for mounting and replacement of the needle assembly. O-rings 60 can seal the cooling fluid pathway.

Figure 13A:
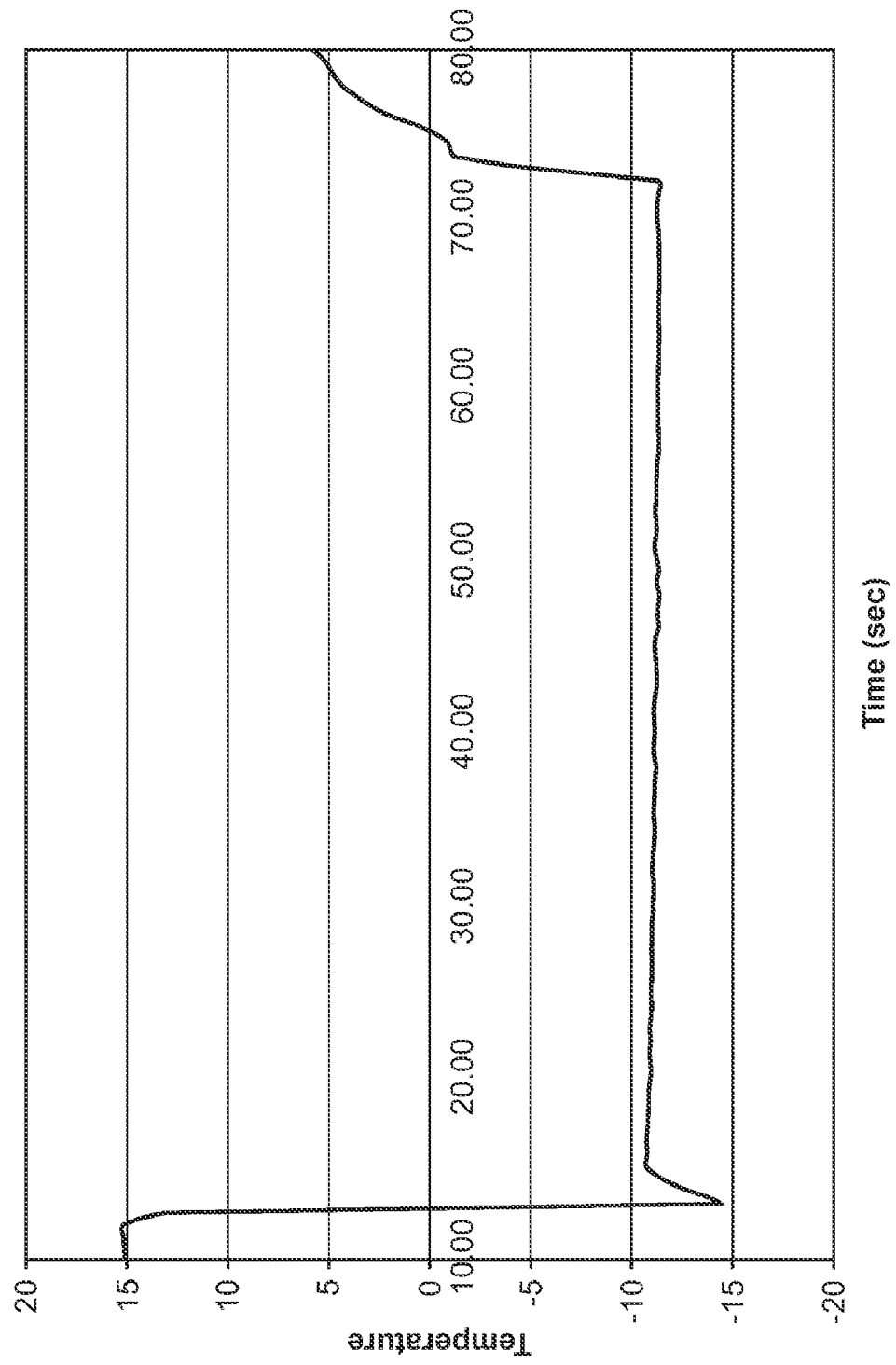
FIGS. 13A-13D graphically illustrate effects of changes in exhaust volume on the cooling response by a small cryogenic needle probe.
Figure 13B:
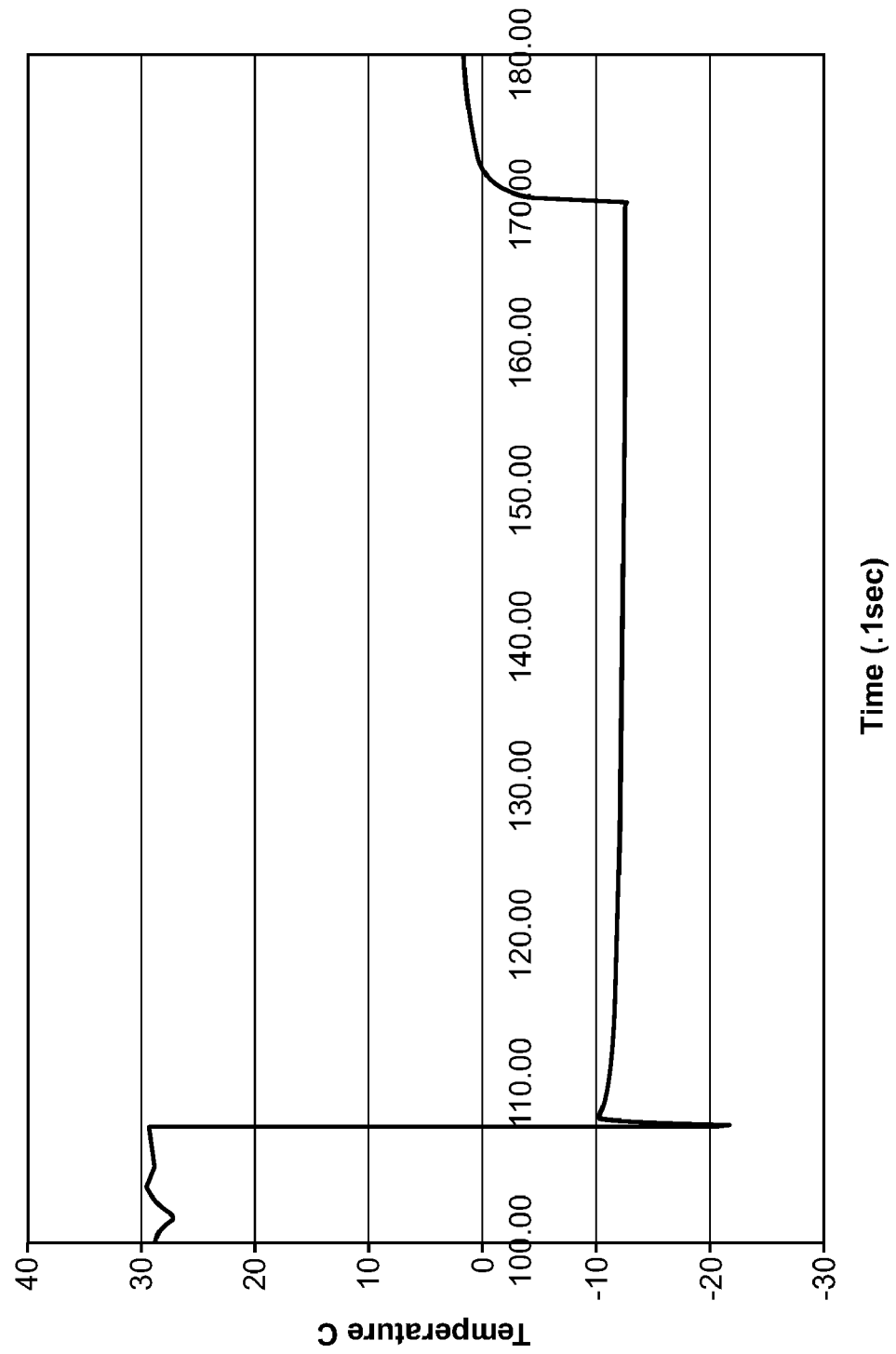
Figure 13C:
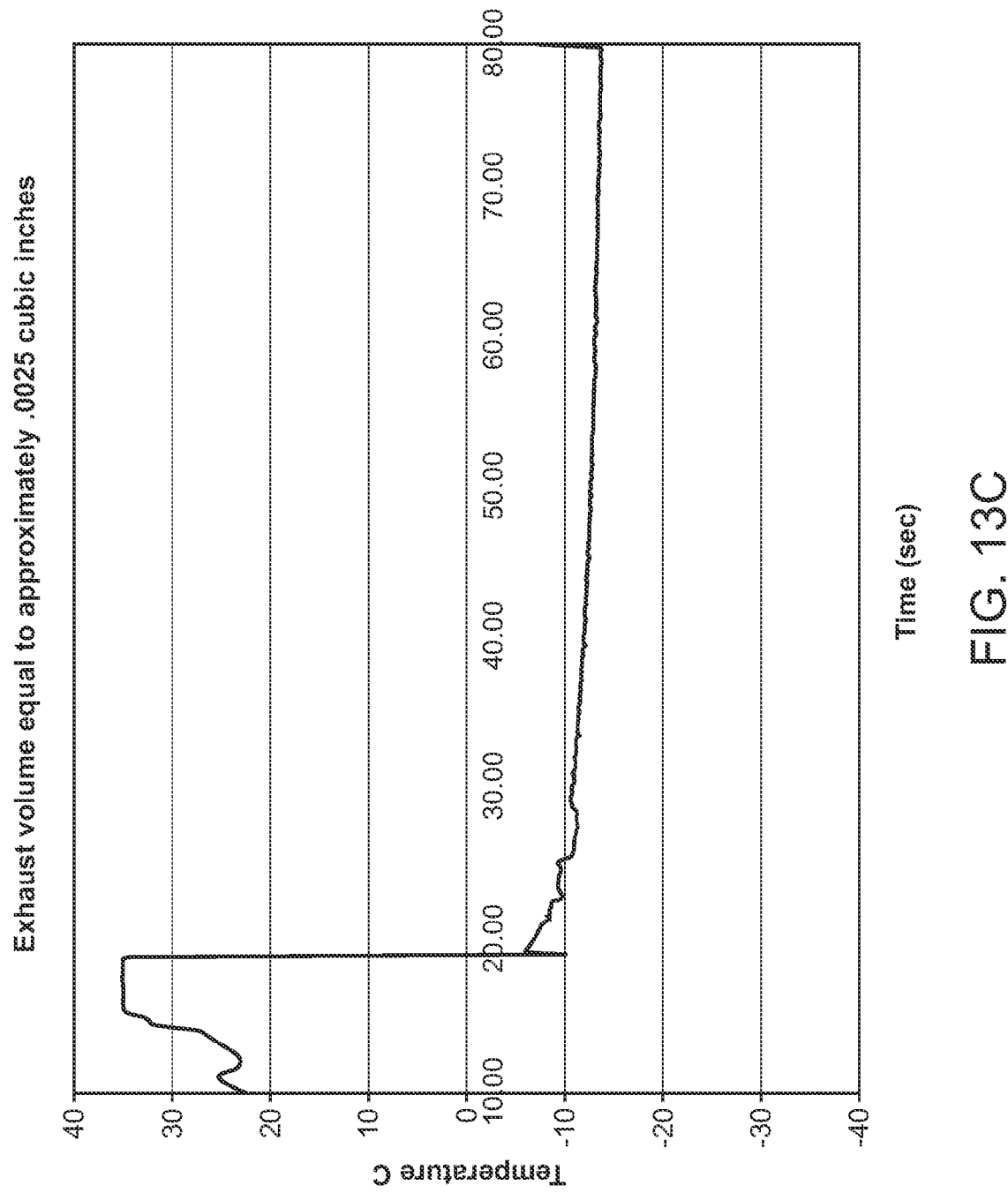
Figure 13D:
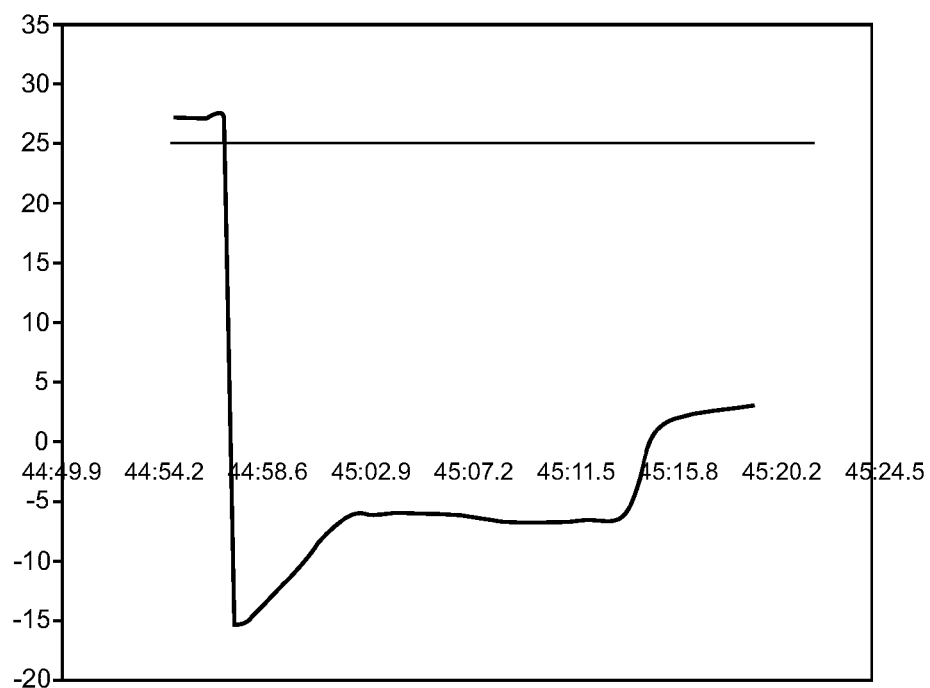

FIGS. 13A-13C present additional details on the effects of exhaust volume on cooling transients. In each case, a graph of temperature over time is shown for the outside temperature of an in vivo 30g cooling needle with a target temperature of about −12° C. The devices were constructed with different exhaust volumes, with the volume being greater than about 0.009 in$^3$ in the embodiment of FIG. 13A. The embodiment of FIGS. 13B and 13C had exhaust volumes of about 0.009 in$^3$ and about 0.0025 in$^3$, respectively. The data collection rate was about 0.7 sec for the embodiment of FIG. 13A, while the embodiments of FIGS. 13B and 13C both had data collection rates of about 0.1 sec, so that the actual nadir for the embodiment of FIG. 13A may have actually been significantly lower than that shown. Regardless, the exhaust volume is preferably less than about 0.05 in$^3$, typically being less than 0.01 in$^3$ and/or 0.009 in$^3$, and ideally being less than 0.005 in$^3$.

Alternative methods to inhibit excessively low transient temperatures at the beginning of a refrigeration cycle might be employed instead of or together with the limiting of the exhaust volume. For example, the supply valve might be cycled on and off, typically by controller 22, with a timing sequence that would limit the cooling fluid flowing so that only vaporized gas reached the needle lumen (or a sufficiently limited amount of liquid to avoid excessive dropping of the needle lumen temperature). This cycling might be ended once the exhaust volume pressure was sufficient so that the refrigeration temperature would be within desired limits during steady state flow.

Figure 5A:
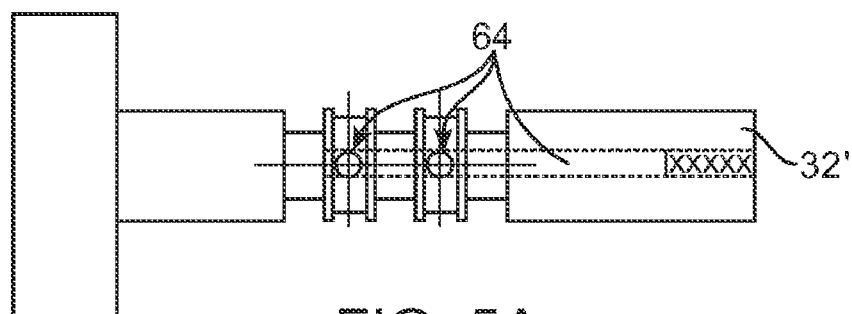
FIGS. 5A-5C illustrate an exemplary supply valve for use in the probe and system of FIGS. 1A and 1B.
Figure 5B:
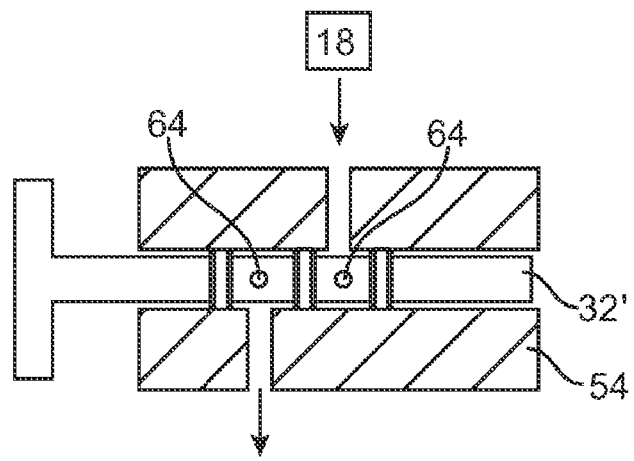
Figure 5C:
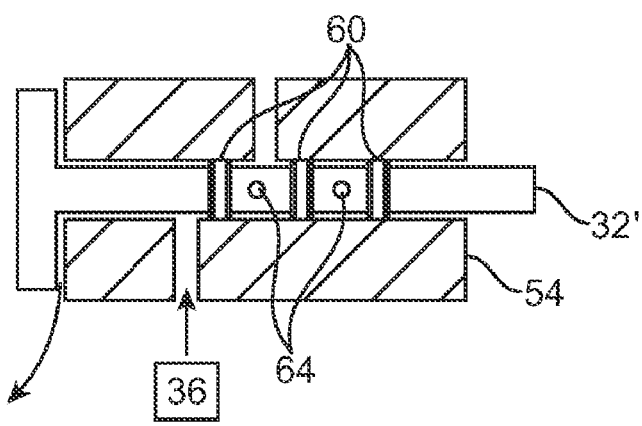

Additional aspects of the exemplary supply valves 32 can be understood with reference to FIGS. 2, 3, and 5A-5C. In FIG. 3, the valve is shown in the "on" configuration, with O-rings 60 sealing either side of the cooling fluid flow path and the cooling fluid flowing around the movable valve member. In FIGS. 5A-5C, the cooling fluid flows through a passage 64 that extends axially along an alternative valve body of valve body 32' when the valve is in the on configuration (seen in FIG. 5B), with the O-rings being disposed between recesses in the movable valve body so as to allow the valve to operate when the valve body is in any rotational orientation about its axis. In both embodiments, the cooling fluid flow path downstream of the valve is vented when the valve is in the "off" configuration (in the embodiment of FIG. 3, by channel 66, and in the embodiment of FIGS. 5A-5C by the vaporizing cooling fluid flowing through the annular space between the valve body and the adjacent housing 54 so as to preserve the cooling fluid within the movable valve body).

Venting of the cooling fluid from the cooling fluid supply tube 36 when the cooling fluid flow is halted by supply valve 32, 32' is advantageous to provide a rapid halt to the cooling of needle 26. For example, a 2.5 cm long 30 g needle cooled to an outside temperature of −15° C. might use only about 0.003 g/sec of nitrous oxide after the system approaches or reaches steady state (for example, 10 seconds after initiation of cooling). If the total volume along the cooling fluid path from supply valve to the distal end or release port of supply tube 36 is about 0.1 cc, the minimum time to flow all the vaporizing liquid through the supply tube might be calculated as follows:

0.1 cc*(0.7 g/cc)=0.07 g of liquid nitrous oxide, 0.07 g/(0.003 g/sec)=23 sec.

Figure 10:
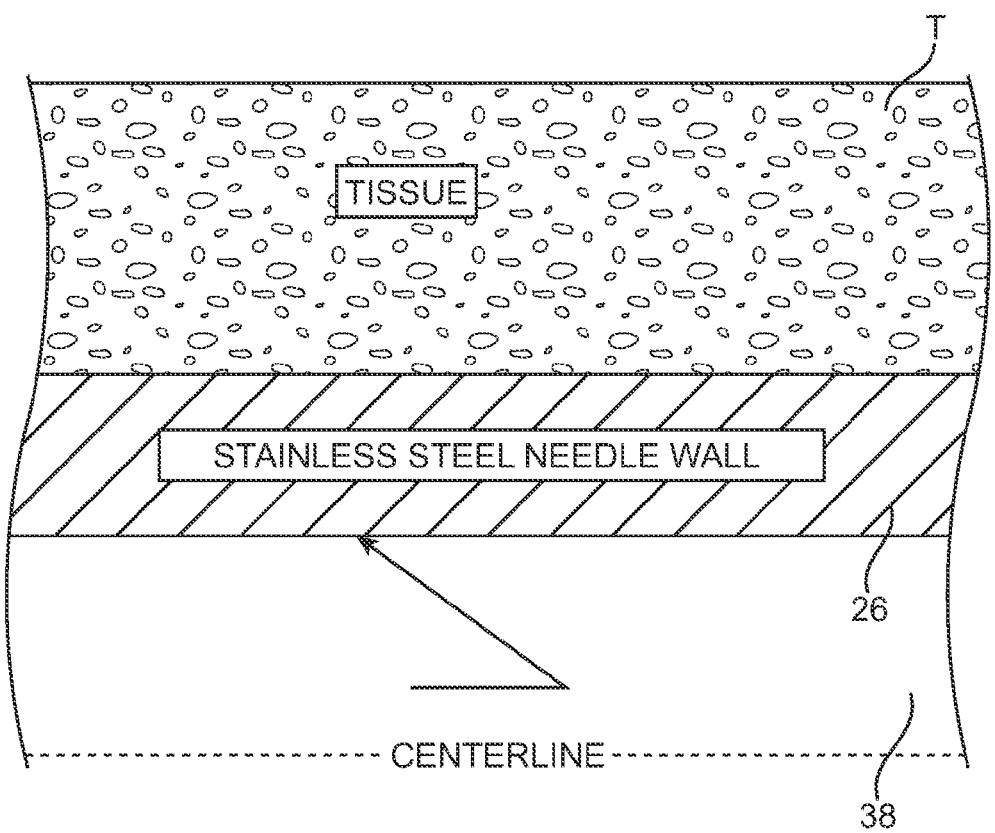
FIG. 10 schematically illustrates a thermal model of a cryogenic microprobe needle.
Figure 10A:
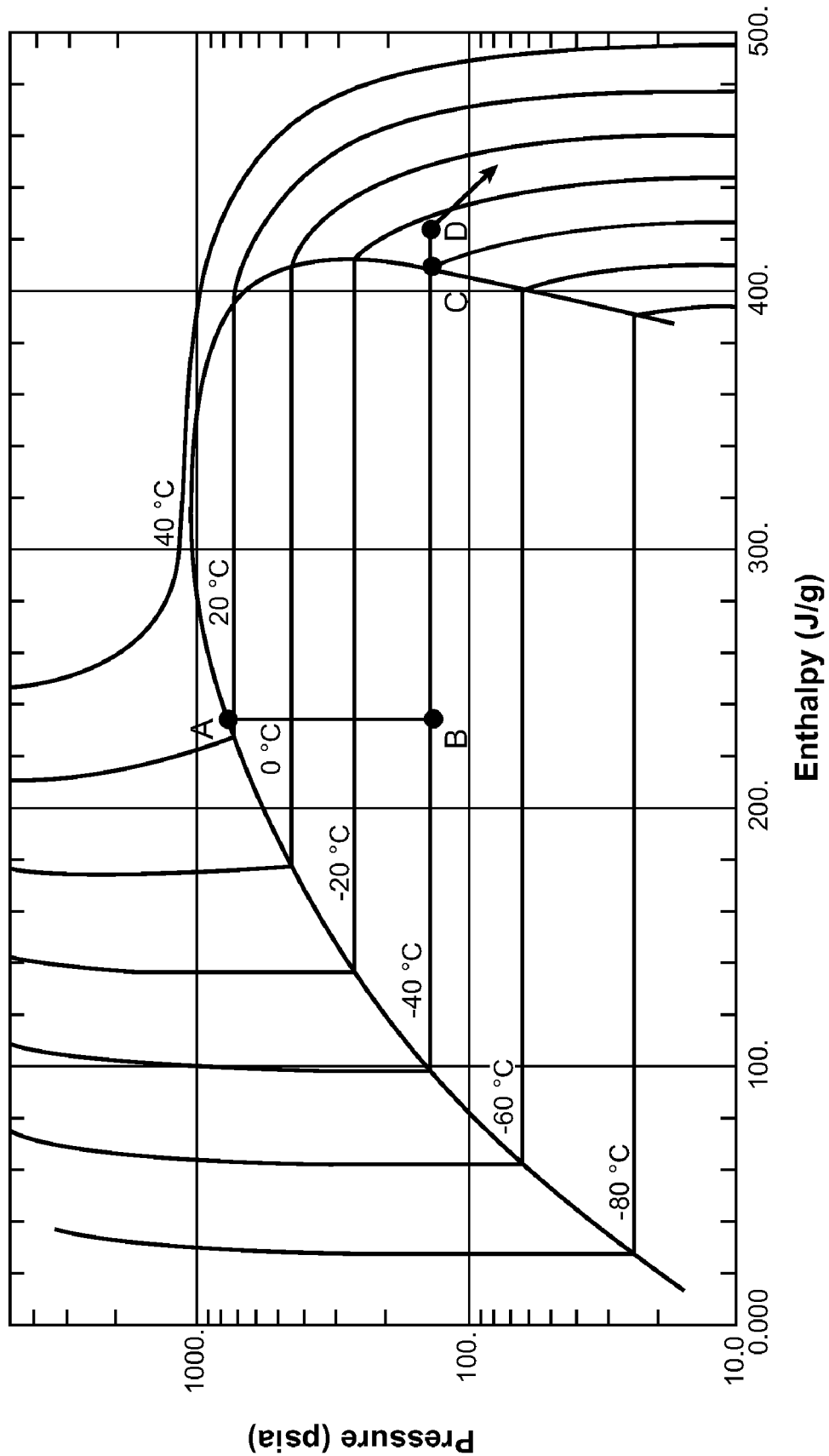
FIGS. 10A-10C graphically illustrate aspects of cryogenic cooling using nitrous oxide in the microprobe needles described herein.
Figure 10B:
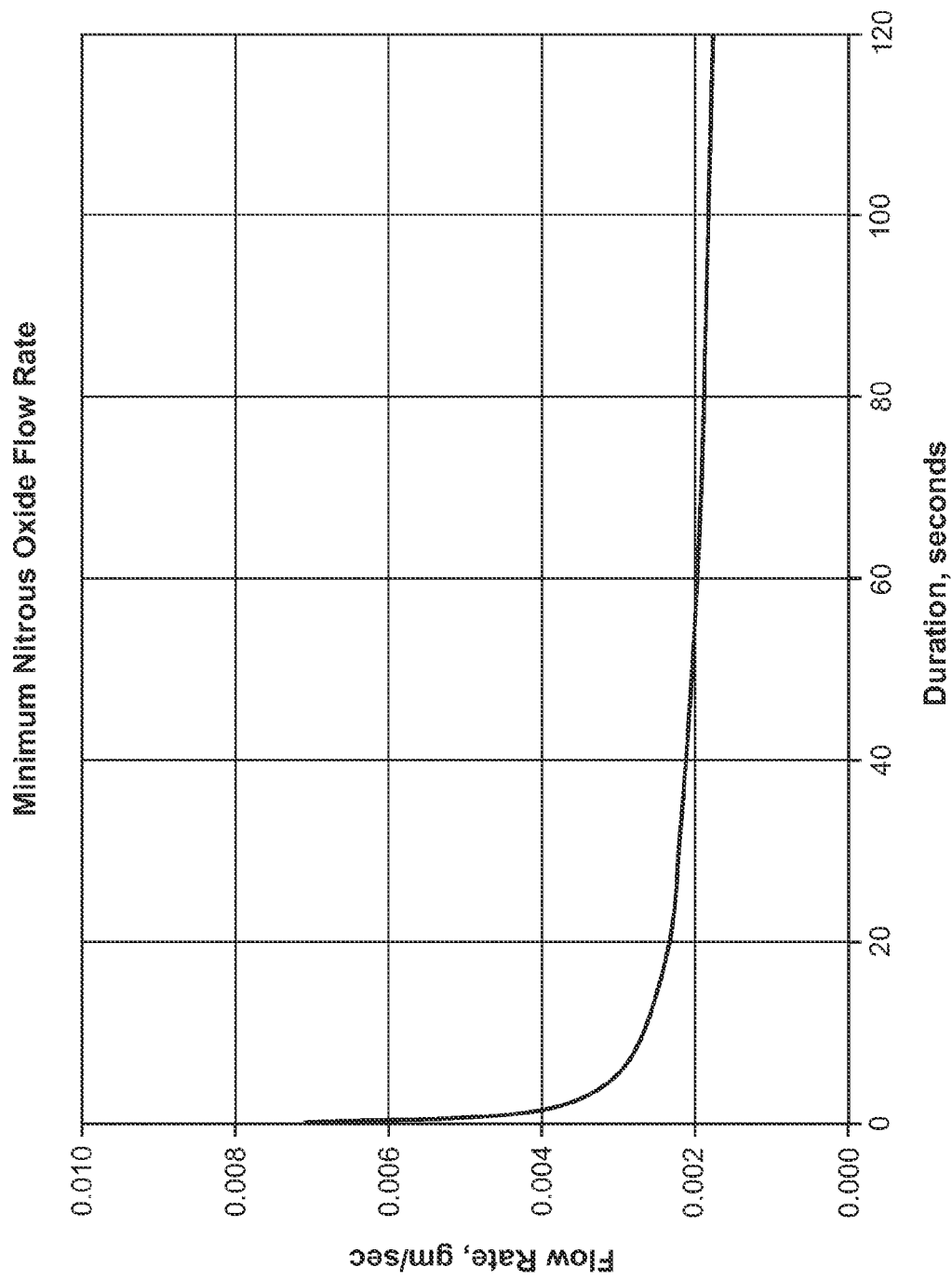
Figure 10C:
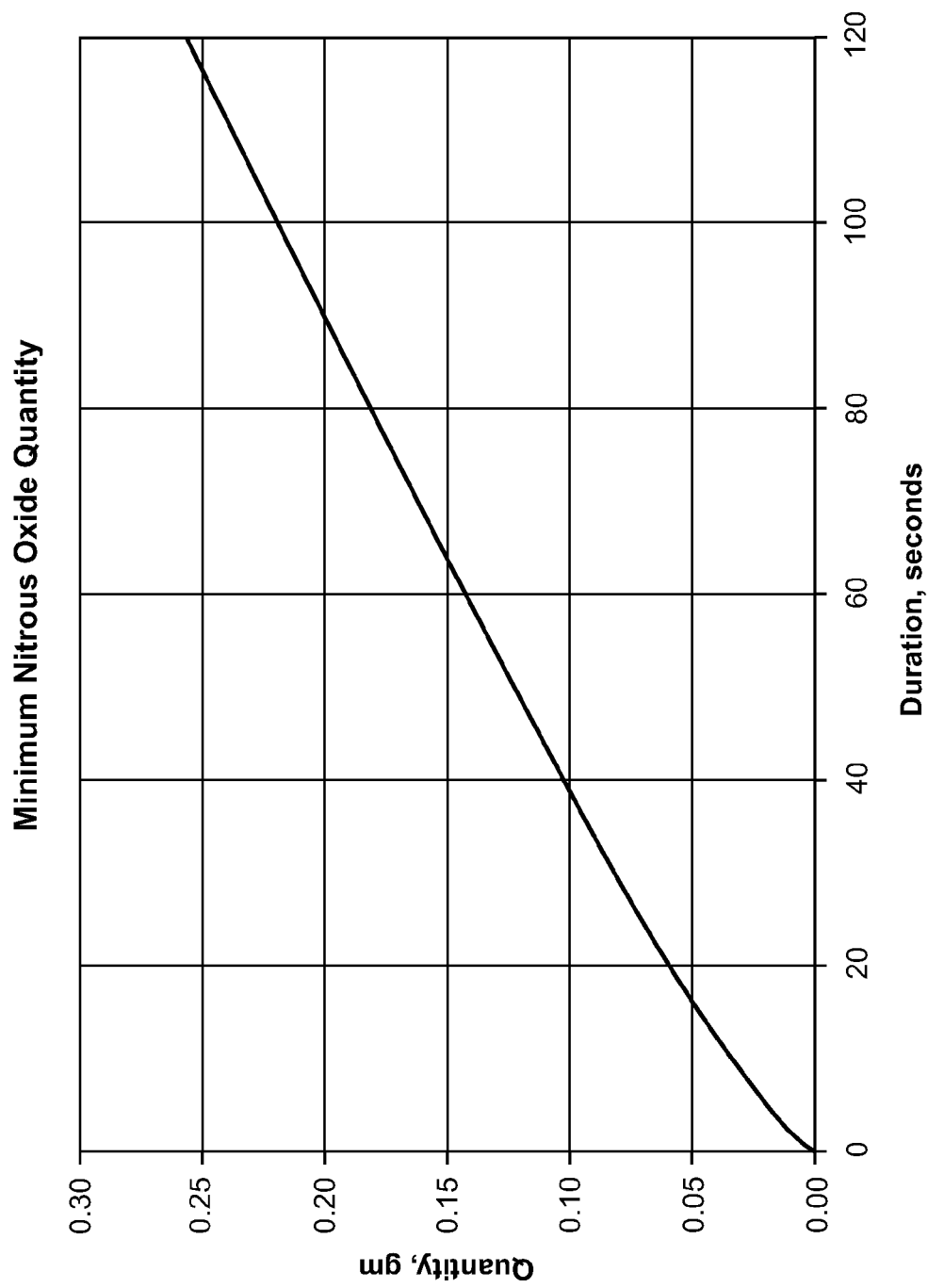

These calculation assume a fused silica supply tube sized to allow the minimum flow of nitrous oxide when fluid supply has a pressure of about 900 psi. When the supply valve is shut off, the pressure on the needle side of the supply valve would decay, causing the actual residual run time to be longer, with only a partial cooling near the distal tip of needle 16. Regardless, it is desirable to limit the flow of cooling fluid into the needle to or near that which will vaporize in the needle so as to facilitate use of a simple disposable cooling fluid supply cartridge 18. Analytical models that may be used to derive these cooling flows include that illustrated in FIG. 10, which may be combined with the properties of the cooling fluid (such as the pressure/enthalpy diagram of nitrous oxide seen in FIG. 10A) and the thermal properties of tissue shown in Table I to determine theoretical minimum cooling fluid flow rates (see FIG. 10B), theoretical minimum cooling fluid quantities (see FIG. 10C), and the like.

TABLE I

| Property | Units | Value |
| --- | --- | --- |
| Upper temperature bond of freezing ($T_2$) | ° C. | −1 |
| Peak of phase transition temperature ($T_3$) | ° C. | −3 |
| Lower Temperature bond of freezing ($T_1$) | ° C. | −8 |
| Thermal conductivity in unfrozen region ($k_u$) | W/(mm-° C.) | 0.00063 |
| Thermal conductivity in frozen region ($k_f$) | W/(mm-° C.) | 0.00151 |
| Volumetric specific heat in unfrozen region ($\{\rho_t c_t\}_f$) | J/(mm³-° C. | 0.00316 |
| Volumetric specific heat in frozen region ($\{\rho_t c_t\}_f$) | J/mm³-° C. | 0.00193 |
| Latent heat of solidification (HF) | J/mm³ | 0.300 |

Referring now to FIGS. 3 and 4, a wide variety of alternative embodiments and refinements may be provided. Fluid supply 18 may be initially opened for use by penetrating a frangible seal of the cartridge with a pierce point 70 (such as by tightening a threaded cartridge support coupled to housing 54), with the nitrous being filtered by a filter 72 before being transmitted further along the cooling fluid path. Suitable filters may have pore sizes of from about 6 to about 25 µm, and may be available commercially from Porex of Georgia (or a variety of alternative suppliers), or may comprise a fine stainless steel screen (such as those having a mesh size of 635 with 0.0009" wire and spacing between the wire edges of approximately 0.0006"), or the like. A wide variety of epoxy or other adhesives 74 may be used, and the replaceable needle housing 24A and other structural components may comprise a wide variety of metals or polymers, including brass or the like. Fins 76 may be included to help vaporize excess cooling liquid traveling proximally of the insertable length of needle 26.

Very fine needles will typically be used to deliver to cooling at and/or below the surface of the skin. These needles can be damaged relatively easily if they strike a bone, or may otherwise be damaged or deformed before or during use. Fine needles well help inhibit damage to the skin during insertion, but may not be suitable for repeated insertion for treatment of numerous treatment sites or lesions of a particular patient, or for sequential treatment of a large area of the patient. Hence, the structures shown in FIGS. 1B, 3, and 4 allow the use probe bodies 16, 54 with a plurality of sequentially replaceable needles. O-rings 60 help to isolate the cooling fluid supply flow (which may be at pressures of up to about 900 psi) from the exhaust gas (which may be at a controlled pressure in a range between about 50 and 400 psi, depending on the desired temperature). Exemplary O-rings may comprise hydrogenated Buna-N O-rings, or the like.

Figure 11B:
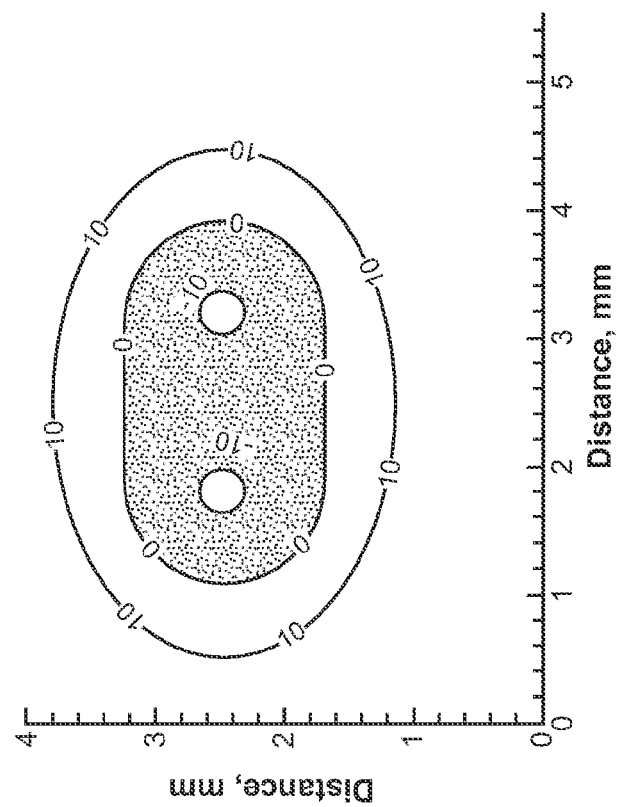
FIGS. 11A and 11B schematically illustrate cross-sectional views cooling with a one needle system and a multiple needle system.
Figure 11A:
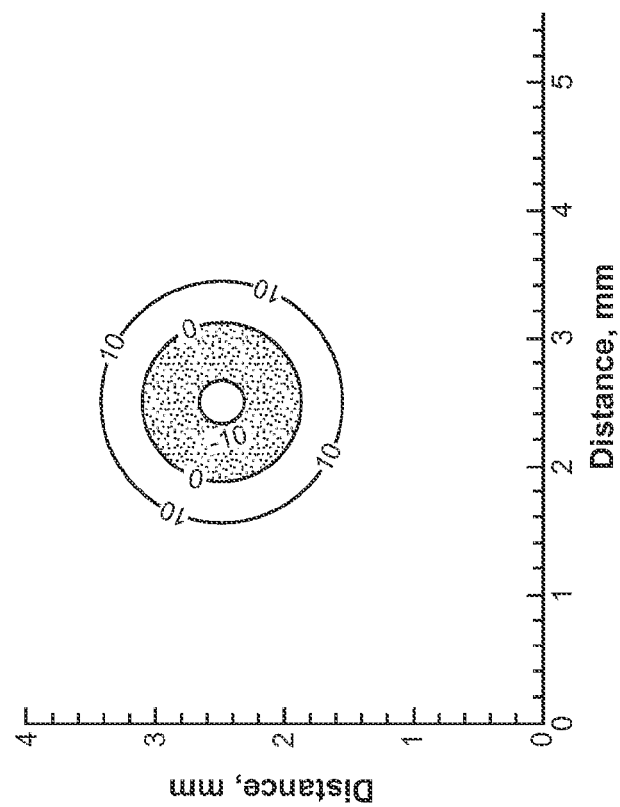

It may be advantageous to increase the volume of tissue treated by a single treatment cycle. As it is often desirable to avoid increasing the needle size excessively, along with selecting needles of different lengths, needle assemblies having differing numbers of needles in a needle array may also be selected and mounted to the probe body. Other embodiments may employ a single needle array fixedly mounted to the probe body, or a plurality of replaceable needle assemblies which all include the same number of needles. Regardless, cooling fluid flow to a plurality of needles may be provided, for example, by inserting and bonding a plurality of fused silica supply tubes into a 0.010 polyimide tubing 58 or header within the needle assembly, and by advancing the distal end of each supply tube into a lumen of an associated needle 26. The needles might vent into a common exhaust space coaxially around polyimide tubing 58 in a manner similar to the single needle design shown. This can increase the quantity of tissue treated adjacent and/or between needles, as can be seen by comparing the theoretical 15 second exposures to one and two needles having a −15° C. probe surface, as shown in FIGS. 11A and 11B, respectively.

Figure 6:
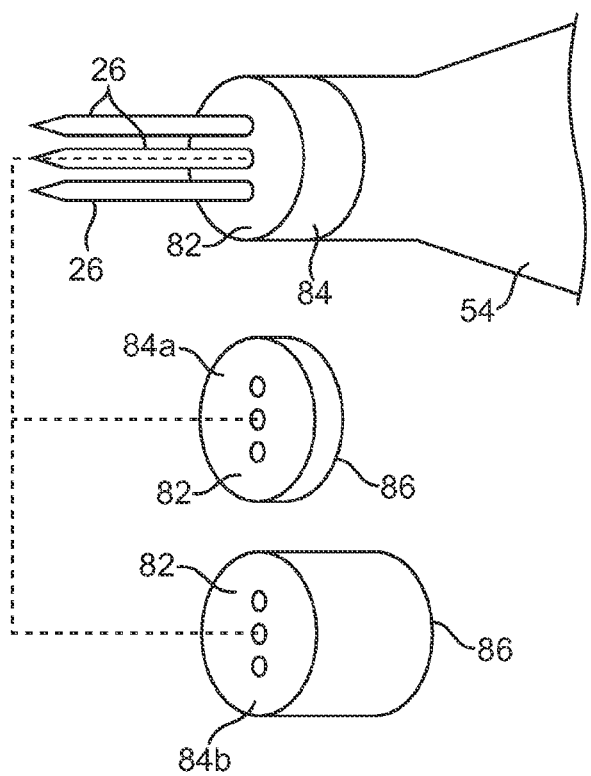
FIGS. 6-8 illustrate skin-engaging surfaces that selectably limit an effective insertable length of the needle, that apply pain-dulling pressure, and that apply inflammation-inhibiting cooling to the skin before and/or during treatment of the target tissue, respectively.

Referring now to FIG. 6, it may be desirable to allow a system user to select a treatment depth, and/or to treat the skin surface to a temperature similar to that of the underlying target tissue along needle 26. A distally oriented surface 82 supported by probe body 54 adjacent and/or around the proximal end of the needles may be configured to limit heat transfer to or from the skin when the needle 26 is inserted so that surface 82 engages the skin and cooling fluid flows into the needle. Exemplary heat transfer limiting surfaces may be formed, for example, from a small rigid foam pad or body 84. Closed cell polyethylene foam or Styrofoam™ foam bodies may be used. As seen in FIG. 6, an alternatively selectable set of bodies may also have differing thicknesses between the skin engaging-surface 82 and a surface 86 that engages the distal portion of the probe body. A user can then select an insertable length of the needle by selecting an appropriate probe body 84, 84a, 84b and mounting the selected probe body onto the needles. Skin engaging surface 82 of bodies 84, 84a, and 84b (or some other skin engaging surface adjacent the distal end of the needle) may be used to apply pressure to the skin, lesion, and/or target tissue during treatment. Alternative insertable length varying arrangements may also be provided, including those having threaded or other articulatable structures supporting the skin engaging surface 82 relative to the adjacent probe body 54 and the like.

Figure 7:
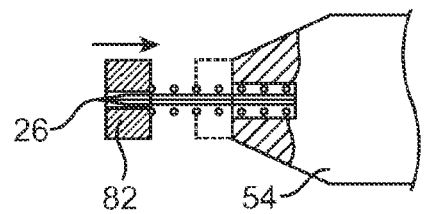

Referring now to FIG. 7, the application of pressure before, during, and/or after cooling may help dull or otherwise inhibit sharp pain. Such pain may otherwise result from the skin penetration, cooling, or thawing of the target and/or collateral tissues. It may also be beneficial to obscure the patient's view of the cooling needles, and/or to cover the needles when not in use so as to inhibit needle-stick injuries and potential disease transmission. Toward that end, skin-engaging surface 82 may be supported by an articulatable support structure having a first configuration (shown in solid in FIG. 7) and a second configuration (shown dashed in FIG. 7). A simple spring mechanism may be used to apply a desired contact force between the skin-engaging surface 82 and the patient before insertion and during cooling. More sophisticated arrangements can also be employed in which the needle is driven distally and then proximally relative to the skin engaging surface appropriate times after sufficient pressure is applied to the patient, and the like.

Figure 8:
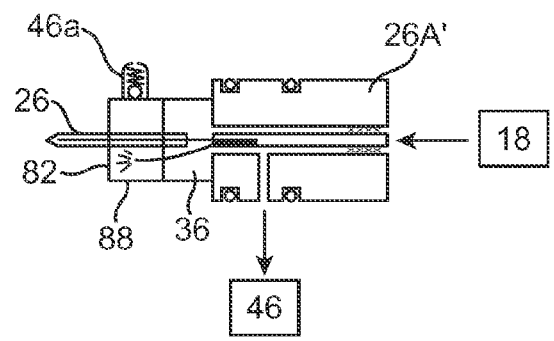
Figure 14:
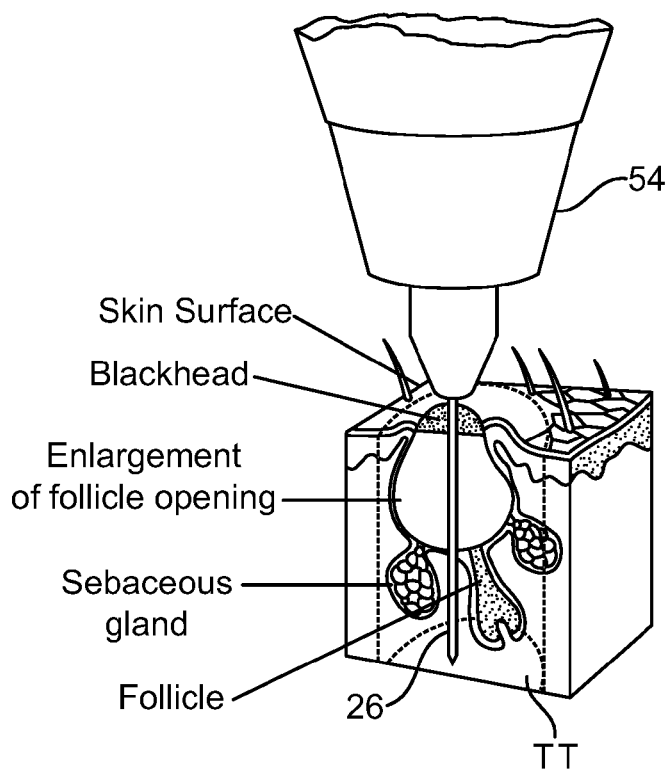
FIG. 14 schematically illustrates a cryogenic microprobe needle system being used for a dermatological treatment.

Referring now to FIG. 8, still further alternative embodiments may be provided, in this case to apply different cooling temperatures to the patient, and/or to apply cooling to the skin surface and to a target tissue adjacent needle 26. For example, in the case of acne it may be desirable to have two different cooling target temperatures, with cooling on the skin surface to inhibit inflammation (such as to about −10° C.), and (see FIG. 14) cooling of a target tissue TT cylinder around needle 26 sufficient to kill bacteria in the sebaceous gland and enlarged follicle opening (such as to about −20° C.). This dual temperature treatment may be particularly beneficial for severe forms of acne involving cysts or nodules. To provide cooling of tissue engaging surface 82, that surface may be thermally coupled to a chamber 88. Cooling fluid may be transmitted into chamber 88 by a port of a cooling fluid supply tube 36, and the pressure of chamber 88 (and hence the temperature within the chamber) can optionally be controlled by a dedicated additional pressure relief valve 46a. As the pressure within chamber 88 may differ from that within the needle, different treatment temperatures may be provided. The structures described herein can also be combined, for example, with the dual skin surface/needle temperature treatment structure of FIG. 8 being compatible with the replaceable needle systems of FIGS. 1B, 3, and/or 4. The dual skin surface/needle treatment systems and methods may also be compatible, for example, with the articulatable skin surface supports of FIG. 7 so as to apply cooled pressure to the skin prior to and/or during needle insertion using a flexible fluid supply tube or the like.

Still further alternatives may also be provided, including systems that generate a high rate of cooling to promote necrosis of malignant lesions or the like. High cooling rates limit osmotic effects in the target tissue. Slow cooling may tend to promote ice formation between cells rather than within cells due to the osmotic effect. While such slow cooling can be provided where necrosis is not desired (such as through the use of a proportion supply valve to modulate flow, a processor generated on/off cycle during initial cooling, or the like), the needle probes described herein will often be well suited to induce rapid cooling rates of the target tissue by vaporizing the cooling fluid in close thermal and spatial proximity to that target tissue. Hence, where necrosis of cells by intracellular ice formation is desired, cooling rates of about 25° C./sec or more, or even about 50° C./sec or more can be provided.

Figure 9:
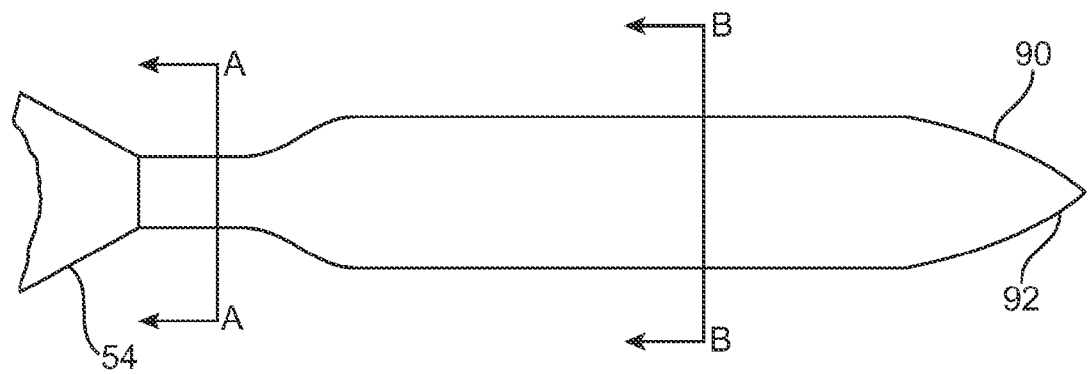
FIGS. 9, 9A, and 9B schematically illustrate a needle having an elongate cross-section to enhance the volume of treated tissue.
Figure 9A:
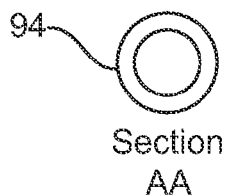
Figure 9B:
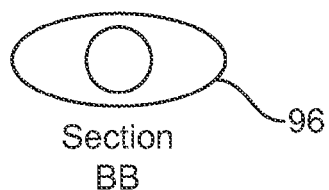

Referring now to FIGS. 9, 9A, and 9B, needles having circular cross-sectional shapes can often be used, but may not always provide the desired surface area for the cross-sectional area of the needle. Increased surface area may decrease the amount of time the needle is inserted to cool a volume of tissue to a temperature in a target range. Hence, a needle with an elongate outer cross-section such as elliptical needle 90 may be desirable. A distal cutting edge 92 at the distal tip may facilitate insertion and a circular cross-section 94 near the proximal end may limit cooling adjacent the skin, while cooling of the target tissue therebetween is enhanced by elliptical cross-section 96.

Referring now to FIG. 15, a method 100 facilitates treating a patient using a cryogenic cooling system having a self-contained disposable handpiece and replaceable needles such as those of FIG. 1B. Method 100 generally begins with a determination 110 of the desired tissue remodeling and results, such as the alleviation of specific cosmetic wrinkles of the face, the inhibition of pain from a particular site, the alleviation of unsightly skin lesions or cosmetic defects from a region of the face, or the like. Appropriate target tissues for treatment are identified 112 (such as the subdermal muscles that induce the wrinkles, a tissue that transmits the pain signal, or the lesion-inducing infected tissues), allowing a target treatment depth, target treatment temperature profile, or the like to be determined 114. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

As described above, pressure, cooling, or both may be applied 118 to the skin surface adjacent the needle insertion site before, during, and/or after insertion 120 and cryogenic cooling 122 of the needle and associated target tissue. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply cartridge included in the self-contained handpiece is depleted, the used handpiece and needles can be disposed of 130.

A variety of target treatment temperatures, times, and cycles may be applied to differing target tissues to as to achieve the desired remodeling. For example, (as more fully described in patent application Ser. No. 11/295,204, previously incorporated herein by reference) desired temperature ranges to temporarily and/or permanently disable muscle, as well as protect the skin and surrounding tissues, may be indicated by Table TI as follows:

TABLE II

| Temperature | Skin | Muscle/Fat |
|---|---|---|
| 37° C. | baseline | baseline |
| 25° C. | cold sensation | |
| 18° C. | reflex vasodilation of deep blood vessels | |
| 15° C. | cold pain sensation | |
| 12° C. | reduction of spasticity | |
| 10° C. | very cold sensation reduction of chronic oedema Hunting response | |
| 5° C. | pain sensation | |
| 0° C. | freezing point | |
| −1° C. | | Phase transition begins |
| −2° C. | | minimal apoptosis |
| −3° C. | | Peak phase transition |
| −5° C. | tissue damage | moderate apoptosis |
| −8° C. | | Completion of phase transition |
| −10° C. | | considerable apoptosis |
| −15° C. | | extensive apoptosis mild-moderate necrosis |
| −19° C. | | adoptosis in some skeletal muscle tissues |
| −40° C. | | extensive necrosis |

To provide tissue remodeling with a desired or selected efficacy duration, tissue treatment temperatures may be employed per Table III as follows:

TABLE III

| Cooled Temperature Range | Time Effectiveness | Purpose |
| --- | --- | --- |
| ≧0° C. | Treatment lasts only while the needle is inserted into the target tissue. | Can be used to identify target tissues. |
| From 0° C. to −5° C. | Often lasts days or weeks, and target tissue can repair itself. Embodiments may last hours or days. | Temporary treatment. Can be used to evaluate effectiveness of remodeling treatment on skin surface shape or the like. |
| From −5° C. to −15° C. | Often lasts months to years; and may be permanent. Limited muscle repair. Embodiments may last weeks to months. | Long term, potentially permanent cosmetic benefits. Can be deployed in limited doses over to time to achieve staged impact, controlling outcome and avoiding negative outcome. May be employed as the standard treatment. |
| From −15° C. to −25° C. | Often lasts weeks or months. Muscle may repair itself via satellite cell mobilization. Embodiments may last years. | May result in Mid-term cosmetic benefits, and can be used where permanent effects are not desired or to evaluate outcomes of potentially permanent dosing. Embodiments may provide permanent treatment. |

There is a window of temperatures where apoptosis can be induced. An apoptotic effect may be temporary, long-term (lasting at least weeks, months, or years) or even permanent. While necrotic effects may be long term or even permanent, apoptosis may actually provide more long-lasting cosmetic benefits than necrosis. Apoptosis may exhibit a non-inflammatory cell death. Without inflammation, normal muscular healing processes may be inhibited. Following many muscular injuries (including many injuries involving necrosis), skeletal muscle satellite cells may be mobilized by inflammation. Without inflammation, such mobilization may be limited or avoided. Apoptotic cell death may reduce muscle mass and/or may interrupt the collagen and elastin connective chain. Temperature ranges that generate a mixture of these apoptosis and necrosis may also provide long-lasting or permanent benefits. For the reduction of adipose tissue, a permanent effect may be advantageous. Surprisingly, both apoptosis and necrosis may produce long-term or even permanent results in adipose tissues, since fat cells regenerate differently than muscle cells.

Figure 16:
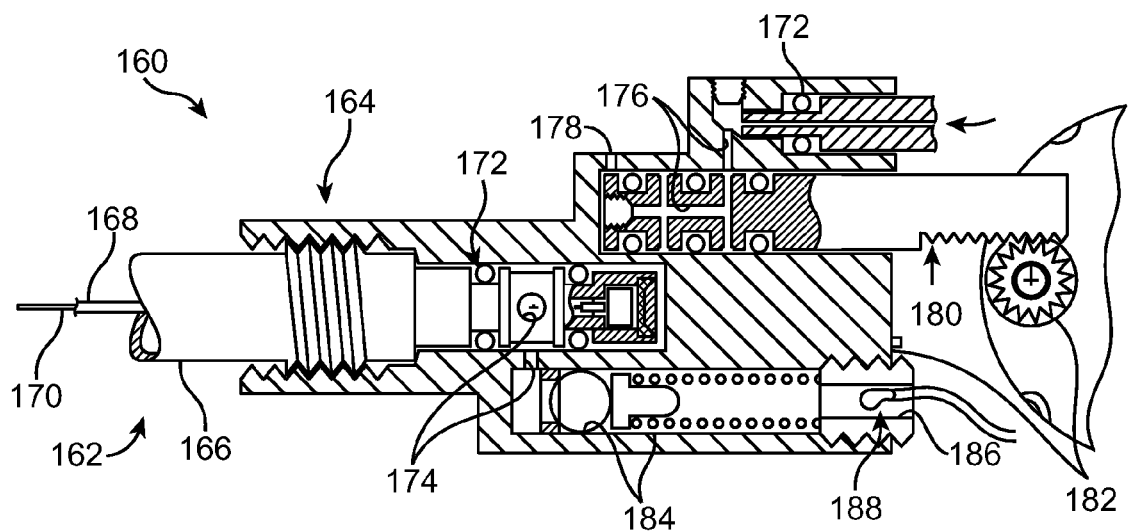
FIG. 16 is a schematic cross-sectional view showing an alternative exemplary needle interface, along with the adjacent structures of the needle assembly and probe body.

Referring now to FIG. 16, an exemplary interface 160 between a cryogenic cooling needle probe 162 and the associated probe body structure 164 are illustrated, along with adjacent portions of the needle, valve, probe body, and the like. Needle probe 162 is included in a needle assembly having a needle hub 166 with a lumen containing a polyimide tube 168 around a fused silica cooling fluid supply tube with its polyimide jacket 170. O-rings 172 seal in exhaust gas path 174 and inlet cooling fluid path 176, with the inlet path having a vent 178 to minimize run-on cooling when the cooling fluid supply is shut off by a valve 180, as generally described above. The valve is here actuated by a motor 182, while the exhaust gas pressure is controlled using a biasing spring and ball valve 184 as described above. A hollow set screw 186 can be used to assemble and/or adjust the pressure relief valve, and a thermistor 188 can be used to sense cooling gas flow.

Figure 17A:
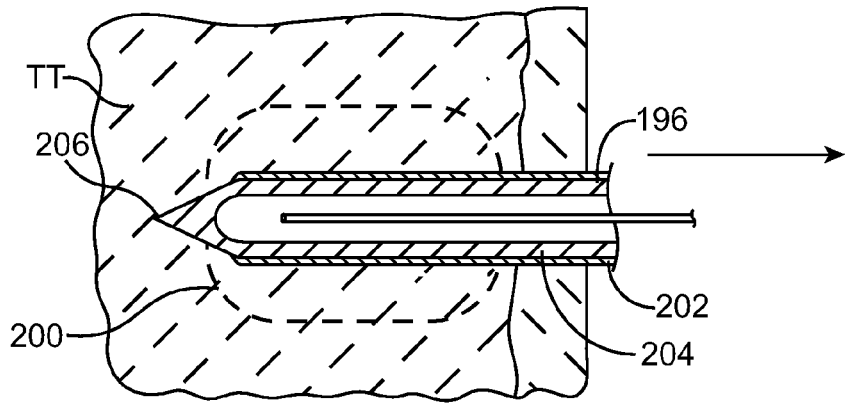
FIGS. 17A and 17B are partial cross-sectional views schematically illustrating removal of a cryogenic cooling probe needle while at least a portion of the tissue remains frozen.
Figure 17B:
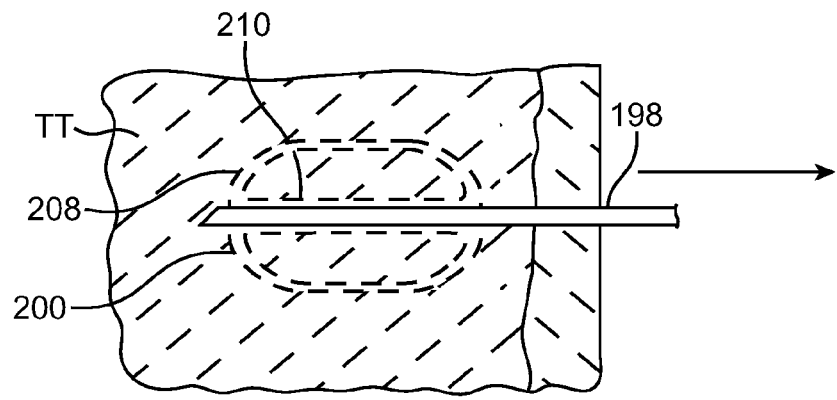

Referring now to FIGS. 17A and 17B, cryogenic cooling probes 196, 198 are inserted into a target tissue TT and a flow of cryogenic cooling fluid is injected into the needle as generally described above. A region 200 of target tissue TT is cooled sufficiently to freeze and effect the desired remodeling of at least a portion of the target tissue. Rather than waiting for the frozen target tissue to thaw, in the embodiment of FIG. 17A a lubricious coating 202 facilitates removal of the needle while at least a portion of the frozen target tissue remains frozen. The lubricious coating 202 may comprise a material having a thermal conductivity which is significantly less than that of the underlying probe structure 204. Coating 202 may have a thickness which is significantly less than that of the underlying probe structure 204, limiting the total insulation effect of the coating, and/or an interior temperature of probe 196 may be reduced so as to provide the desired overall cooling treatment. While it may be counterintuitive to cool the target tissue through a thermally insulating lubricious coating, the ability to more rapidly remove probe 196 from the patient can significantly increase the speed with which procedures may be performed, particularly when a large number of insertion/cooling/removal cycles are involved, and/or when the thaw time is at least half as long as (often being as long as or longer than) the active cooling time.

Note that a small surface 206 of probe 196 may be free of lubricious coating 202. Where the underlying probe structure 204 comprises an electrical conductor such as stainless steel or some alternative metal, the uncovered surface portion 206 may be used as an electrode for neurostimulation during positioning of probe 196 or the like.

In the embodiment of FIG. 17B, the use of cryosurgical probes of small diameter may facilitate removal of the probe without having to wait for a complete thaw of region 200. In this embodiment, microneedle probe 198 has a cross-sectional size of a 20-gauge needle or less, preferably comprising a 25-gauge needle or smaller, and ideally comprising a 30-gauge needle. These small diameter microneedle probes have little thermal mass and can be warmed relatively quickly by conduction from adjacent tissues and/or by any warm fluids flowing therein. As a result, while a major portion 208 of the target tissue remains frozen a layer 210 disposed between the still-frozen region and probe 198 may facilitate safe removal of the probe from the patient. Thawed layer 210 may comprise thawed target tissue, thawed extracellular fluids, or the like. Small needles also have small probe/tissue interface surface areas which may limit the total stiction between the probe and frozen tissue. Regardless of any particular mechanism of action, the use of small diameter cryogenic microneedles may allow safe removal of the probe from a treated tissue in a time which is significantly less than that associated with complete thaw of the iceball that has been formed. Exemplary embodiments using a lubricious coating and/or small diameter probe may allow the probe to be removed within about 10 seconds of the cooling, optionally allowing safe removal within about 5 seconds of cooling or even within about 3 seconds of cooling.

Figure 18A:
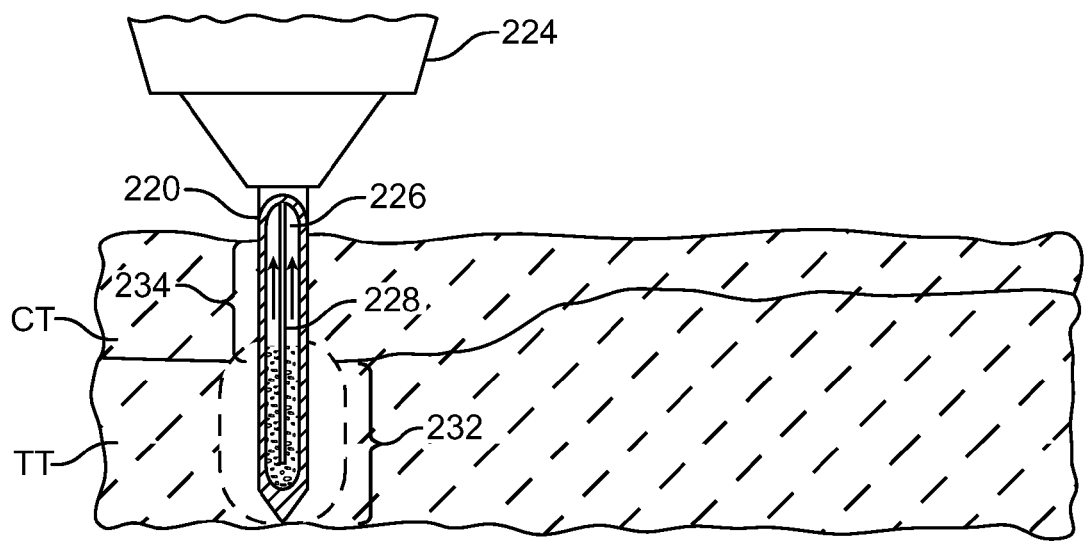
FIGS. 18A and 18B are partial cross-sectional views schematically illustrating how a depletion of liquid from a vaporizing cryogenic cooling fluid can be used to limit an effective treatment length on a portion of a cryogenic probe.
Figure 18B:
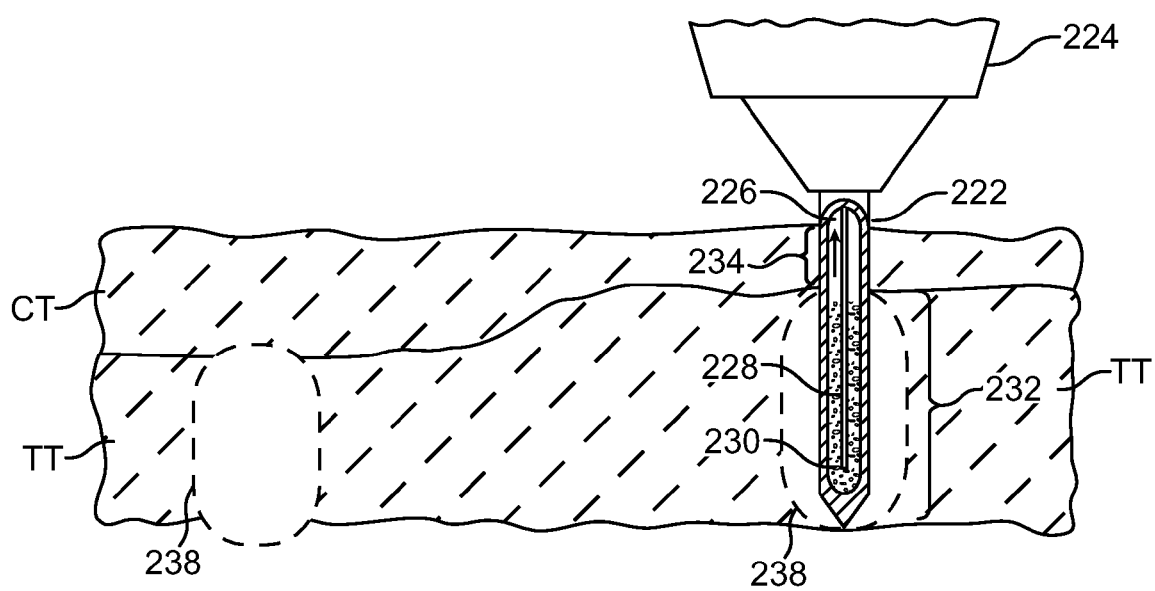

Referring now to FIGS. 18A and 18B, appropriate metering of the cooling fluid into a cryogenic cooling probe 220, 222, can be used to control the length of the probe that applies a therapeutic cooling. Probes 220, 222 are replaceably supported by a probe body 224 via a needle receptacle or interface, as generally described above. Each probe includes a lumen 226 with a cooling fluid supply tube 228 extending to a distal port 230. Through proper selection of the length of the cooling fluid supply tube 228 and/or an inner diameter of the lumen within the supply tube, the supply tube can be used to meter cooling fluid. More specifically, as noted above, cooling of the target tissue TT along a distal portion 232 of probe 228 is cooled by evaporation of the liquid included in the cryogenic cooling fluid. As shown in FIG. 18A, cooling of a collateral tissue CT proximal of the target tissue TT may be limited by controlling the amount of cooling fluid flow so that the vaporizing liquid is depleted by the time the flow reaches a proximal portion 234 of the probe. In the embodiment of FIG. 18B, a greater length of probe 222 is cooled by providing a relatively larger quantity of cooling fluid (and liquid) flowing from the supply tube 238 into lumen 226 via port 230, so that liquid remains present for vaporization throughout a longer distal portion 232 of the probe. Note that the difference in lengths of the cooled portion 232 may be provided despite making use of an outer probe structure that is similar in cross section and/or overall length.

While the proximal portion 234 of probes 220, 222 may be cooled somewhat (via conduction from the distal portion 232 of the probe, from the passage of gas vaporized from the gas of the cooling fluid, or the like), a temperature of collateral tissue CT may remain above the remodeling treatment temperature of a treatment zone 238 within the target tissue. Hence, the collateral tissue may avoid injury despite the absence of any additional insulation on the proximal portion of the probe. This also facilitates the use of differing treatment zones 238 at different locations for a particular patient through the selection of needle assemblies having appropriate cooling fluid supply paths with the desired differing cooling fluid flow characteristics.

While the exemplary embodiments have been described in some detail for clarity of understanding and by way of example, a number of modifications, changes, and adaptations may be implemented and/or will be obvious to those as skilled in the art. For example, one or more temperature feedback loops may be used to control the treatments, with the tissue temperature optionally being taken using a temperature sensing needle having a temperature sensor disposed adjacent an outer cooled skin engaging surface of the needle. Hence, the scope of the present invention is limited solely by the independent claims.

What is claimed is:

1. A method for treating tissue of a patient, the method comprising;
    inserting a first needle through a first insertion point and into a first target region of the tissue by manipulating a handle, the handle supporting the first needle via a needle interface;
    cooling the first target region with the first needle and removing the first needle from the patient;
    replacing the first needle in the needle interface with a second needle;
    inserting the second needle through a second insertion point and into a second target region of the tissue by manipulating the handle; and
    cooling the second target region with the second needle;
    wherein the first needle is included in a first needle assembly, wherein the second needle is included in a second needle assembly, and wherein insertion of the second needle is performed during simultaneous insertion of a plurality of needles of the second needle assembly into the target tissue; and
    wherein each of the plurality of needles of the second needle assembly includes a cooling fluid supply lumen and a vaporization cooling lumen, the cooling fluid supply lumens in fluid communication with a cooling fluid supply of the needle interface, wherein the cooling with the second needle is performed while introducing cooling fluid from the supply lumens into vaporization lumens of each needle, and wherein gas from the vaporization lumens flows to a common pressure-regulated exhaust path.

2. The method of claim 1, wherein the cooling of the tissue with the plurality of needles of the second needle assembly is performed so that the tissue throughout a contiguous treatment zone is cooled to a temperature in a desired remodeling temperature range.

3. The method of claim 1 further comprising disposing of the first and second needles so as to inhibit dull needle insertion.

4. A method for treating tissue of a patient, the method comprising;
    inserting a first needle through a first insertion point and into a first target region of the tissue by manipulating a handle, the handle supporting the first needle via a needle interface;
    cooling the first target region with the first needle and removing the first needle from the patient;
    replacing the first needle in the needle interface with a second needle;
    inserting the second needle through a second insertion point and into a second target region of the tissue by manipulating the handle, the first and second needles each having a sharpened distal tip and a 20 gauge needle size or less;
    cooling the second target region with the second needle; and
    disposing of the first and second needles so as to inhibit dull needle insertion;
    wherein the handle is included in a probe body, the probe body housing a fluid supply cartridge and a battery, and further comprising disposing of the probe body so that the probe body and cartridge are used to treat only the patient.

5. A method for treating tissue of a patient, the method comprising;
    inserting a first needle through a first insertion point and into a first target region of the tissue by manipulating a handle, the handle supporting the first needle via a needle interface;

cooling the first target region with the first needle and removing the first needle from the patient;

replacing the first needle in the needle interface with a second needle;

inserting the second needle through a second insertion point and into a second target region of the tissue by manipulating the handle, the first and second needles each having a sharpened distal tip and a 20 gauge needle size or less;

cooling the second target region with the second needle; and terminating the cooling by closing a cooling fluid shutoff valve disposed along a cooling fluid supply path between a cooling fluid source and a lumen of each needle, wherein the cooling is performed by evaporating cooling fluid within the lumen of the needle, and wherein a volume of the supply path between the valve and the lumen is less than about 0.05 in$^3$ and is vented when the valve is closed; and disposing of the first and second needles so as to inhibit dull needle insertion.

6. The method of claim 4, wherein the second target region is located sufficiently near the first target region for the cooling to cool a contiguous region of the tissue to a temperature within a desired range.

7. The method of claim 4 wherein the first and second target regions comprise first and second lesions, respectively, and wherein the first and second lesions are separated by untreated collateral tissue.

8. The method of claim 1, wherein the first and second needles each have a sharpened distal tip and a 25 gauge needle size or less, and further comprising disposing of the first and second needles so as to inhibit dull needle insertion.

9. A method for treating tissue of a patient, the method comprising;

inserting a first needle through a first insertion point and into a first target region of the tissue by manipulating a handle, the handle supporting the first needle via a needle interface;

cooling the first target region with the first needle and removing the first needle from the patient;

replacing the first needle in the needle interface with a second needle;

inserting the second needle through a second insertion point and into a second target region of the tissue by manipulating the handle, the first and second needles each having a sharpened distal tip and a 20 gauge needle size or less;

terminating the cooling by closing a cooling fluid shutoff valve disposed along a cooling fluid supply path between a cooling fluid source and a lumen of each needle, wherein the cooling is performed by evaporating cooling fluid within the lumen of the needle, and wherein a volume of the supply path between the valve and the lumen is less than about 0.005 in$^3$ and is vented when the valve is closed; and disposing of the first and second needles so as to inhibit dull needle insertion.

10. The method of claim 1, wherein the first needle is included in a first needle assembly having an associated plurality of needles, wherein the second needle is included in a second needle assembly having an associated plurality of needles, and wherein insertion of each of the first and second needle is performed during simultaneous insertion of the associated plurality of needles into the target tissue.

11. A method for treating tissue of a patient, the method comprising;

inserting a first needle through a first insertion point and into a first target region of the tissue by manipulating a handle, the handle supporting the first needle via a needle interface;

cooling the first target region with the first needle and removing the first needle from the patient;

replacing the first needle in the needle interface with a second needle;

inserting the second needle through a second insertion point and into a second target region of the tissue by manipulating the handle; and cooling the second target region with the second needle;

wherein the first needle is included in a first needle assembly having an associated plurality of needles, wherein the second needle is included in a second needle assembly having an associated plurality of needles, and wherein insertion of each of the first and second needle is performed during simultaneous insertion of the associated plurality of needles into the target tissue; and wherein the needles of the assemblies are inserted through skin of the patient so as to ameliorate a cosmetic defect of the patient, wherein the cooling is performed so as to cool tissue below the skin to a treatment temperature in a desired remodeling temperature range, and so that the skin remains warmer than the remodeling temperature range such that visible cooling injury to the skin is inhibited.

12. The method of claim 11, wherein the portions of the needles extending through the skin during the cooling are uninsulated.

13. The method of claim 1, wherein the cooling characteristics of the first needle are associated with a cross-section, a thermal conductivity, and an axial cooling length of the first needle, wherein the cooling characteristics of the second needle are associated with a cross-section, a thermal conductivity, and an axial cooling length of the second needle, and wherein the cross-section, the thermal conductivity, and the axial cooling length of the first needle are the same as the cross-section, the thermal conductivity, and the axial cooling length of the second needle.

14. The method of claim 4, wherein the cooling characteristics of the first needle are associated with a cross-section, a thermal conductivity, and an axial cooling length of the first needle, wherein the cooling characteristics of the second needle are associated with a cross-section, a thermal conductivity, and an axial cooling length of the second needle, and wherein at least one of the cross-section, the thermal conductivity, or the axial cooling length of the first needle are different than a corresponding at least one of the cross-section, the thermal conductivity, or the axial cooling length of the second needle.

* * * * *